(12) United States Patent
Annoura et al.

(10) Patent No.: US 6,706,734 B2
(45) Date of Patent: Mar. 16, 2004

(54) ARYLPIPERIDINOL AND ARYLPIPERIDINE DERIVATIVES AND PHARMACEUTICALS CONTAINING THE SAME

(75) Inventors: Hirokazu Annoura, Nagaokakyo (JP); Kyoko Nakanishi, Ibaraki (JP); Shigeki Tamura, Ibaraki (JP)

(73) Assignee: Daiichi Suntory Pharma Co., Ltd., Tokyo (JP)

( * ) Notice: Subject to any disclaimer, the term of this patent is extended or adjusted under 35 U.S.C. 154(b) by 0 days.

(21) Appl. No.: 10/196,362

(22) Filed: Jul. 17, 2002

(65) Prior Publication Data
US 2003/0130312 A1 Jul. 10, 2003

Related U.S. Application Data

(62) Division of application No. 09/043,563, filed as application No. PCT/JP97/02531 on Jul. 22, 1997, now Pat. No. 6,455,549.

(30) Foreign Application Priority Data
Jul. 22, 1996 (JP) .............................. 8-192123

(51) Int. Cl.[7] .................. A61K 31/4465; C07D 211/22; C07D 211/40
(52) U.S. Cl. ....................... 514/317; 546/192
(58) Field of Search ........................ 546/192; 514/317

(56) References Cited

U.S. PATENT DOCUMENTS

| | | | |
|---|---|---|---|
| 3,301,862 A | 1/1967 | Biel et al. | |
| 3,350,403 A | 10/1967 | Biel | |
| 4,241,071 A | * 12/1980 | Martin et al. | 514/317 |
| 5,019,582 A | 5/1991 | Drejer et al. | |
| 5,723,475 A | 3/1998 | Annoura et al. | |
| 6,048,876 A | 4/2000 | Annoura et al. | |
| 6,455,549 B1 | * 9/2002 | Annoura et al. | 514/327 |

FOREIGN PATENT DOCUMENTS

| | | |
|---|---|---|
| EP | 0 339 579 | 11/1989 |
| EP | 0 494 717 | 7/1992 |
| EP | 0 755 923 | 1/1997 |
| EP | 0 757 986 | 2/1997 |
| FR | 2 706 894 | 12/1994 |
| JP | 53-95963 | 3/1978 |
| JP | 63-126866 | 5/1988 |
| JP | 1-313461 | 12/1989 |
| WO | 95/24390 | 9/1995 |
| WO | 96/22977 | 1/1996 |
| WO | 96/26924 | 6/1996 |

OTHER PUBLICATIONS

Martin et al, *Journal of Medicinal Chemistry*, vol. 22, No. 11, pp. 1347–1354, 1979.
Palmer et al, *Journal of Medicinal Chemistry*, vol. 40, pp. 1982–1989, 1997.
Grundke et al, *Journal of Cardiovascular Pharmacology*, vol. 18, No. 6, pp. 918–925, 1991.
Celkova et al, *Pharmazie*, vol. 52, No. 6, pp. 487–488, 1997.

* cited by examiner

Primary Examiner—Rita Desai
(74) Attorney, Agent, or Firm—Burns, Doane, Swecker & Mathis, L.L.P.

(57) ABSTRACT

A pharmaceutical composition, especially a pharmaceutical composition for the alleviation or treatment of symptoms due to ischemic diseases and symptoms derived from seizures, epilepsy, and migraine, and a $Ca^{2+}$ overload suppressant, containing an arylpiperidinol or arylpiperidine derivative having the formula (I):

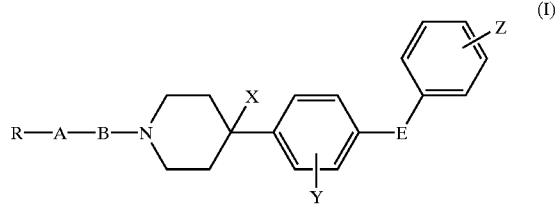

wherein, R is H, an optionally substituted phenyl, an optionally substituted phenoxy, or an optionally substituted benzoyl, A is a connecting bond, a cycloalkylene, or an alkenylene optionally substituted with a lower alkyl, B is an alkylene optionally substituted with OH or an alkoxy or $-NHCO(CH_2)_n-$ where n is an integer of 1 to 5, E is a connecting bond, O, or a methylene, X is OH or H provided that when E is O or a methylene, X is not H, and Y and Z are independently H, a halogen, an alkoxy, or an alkyl optionally substituted with a halogen.

9 Claims, No Drawings

ARYLPIPERIDINOL AND ARYLPIPERIDINE DERIVATIVES AND PHARMACEUTICALS CONTAINING THE SAME

This application is a divisional of U.S. application Ser. No. 09/043,563, filed on Mar. 20, 1998 now U.S. Pat. No. 6,455,949, which was a national stage filing under 35 U.S.C. §371 of International Application No. PCT/JP97/02531 filed on Jul. 22, 1997, which International Application was published by the International Bureau in English on Jan. 29, 1998.

TECHNICAL FIELD

The present invention relates to a pharmaceutical composition for the alleviation or treatment of symptoms due to ischemic diseases, for example, cerebral infarction, intracerebral hemorrhage, transient ischemic attack, subarachnoid hemorrhage, head trauma, after effects of brain surgery, after effects of cerebral arteriosclerosis, and other cerebrovascular disorders, or variant angina, unstable angina, myocardial infarction, cardiovascular system disorders accompanying surgery for revascularization by PTCA (percutaneous transluminal coronary angioplasty)/PTCR (percutaneous transluminal coronary revascularization)/CABG (coronary artery bypass grafting) etc., malignant arrhythmia and myocardial ischemia-reperfusion injury, and further disorders of transplanted organs at the time of organ transplants and temporary blockage of the blood flow in organs at the time of surgery, and also symptoms derived from seizures, epilepsy, migraine, etc. and $Ca^{2+}$ overload suppressants. The present invention further relates to a novel arylpiperidinol and arylpiperidine derivatives having an action in suppressing $Ca^{2+}$ overload and useful for the alleviation or treatment of symptoms due to the above ischemic diseases and also symptoms derived from seizures, epilepsy, migraine, etc., their pharmaceutically acceptable salts, and synthetic intermediates for the preparation of the aforementioned compounds.

BACKGROUND ART

In cellular disorders caused by advanced ischemia, the depletion of ATP, the fall in the pH in the cells, and the destruction of the mechanism for maintenance of the energy-dependent ion homeostasis inside and outside the cell cause the accumulation of a large amount of intracellular divalent Ca ions ($Ca^{2+}$). It is believed that the $Ca^{2+}$ overload causes functional disorders in the mitochondria and randomly activates various enzyme reactions and invites further $Ca^{2+}$ overload to cause a repeated vicious cycle and in the end causes irreparable damage to the cell wall and cell death [F. B. Meyer: Brain Res. Rev., 14, 227 (1989); E. Boddeke et al.: Trends Pharmacol. Sci., 10,397 (1989)].

Pharmaceuticals which suppress cytotoxic $Ca^{2+}$ overload are considered to be these for the alleviation or treatment of various ischemic diseases, for example, cerebral infarction, intracerebral hemorrhage, transient ischemic attack, subarachnoid hemorrhage, head trauma, after effects of brain surgery, after effects of cerebral arteriosclerosis, and other cerebrovascular disorders, or variant angina, unstable angina, myocardial infarction, cardiovascular system disorders accompanying surgery for revascularization by PTCA/PTCR/CABG etc., malignant arrhythmia and myocardial ischemia-reperfusion injury, and further disorders of transplanted organs at the time of organ transplants and temporary blockage of the blood flow in organs at the time of surgery.

DISCLOSURE OF THE INVENTION

Under the above circumstances, the objective of the present invention is to provide a pharmaceutical composition having an action of suppressing cytotoxic $Ca^{2+}$ overload, with high safety, and useful for the alleviation or treatment of symptoms due to ischemic diseases or symptoms derived from seizures, epilepsy, and migraine.

Another objective of the present invention is to provide a novel arylpiperidinol and arylpiperidine derivatives useful as pharmaceutical ingredients, their pharmaceutically acceptable salts, and synthetic intermediates of the same.

In accordance with the present invention, there is provided a pharmaceutical composition for the alleviation or treatment of symptoms due to ischemic diseases or symptoms derived from seizures, epilepsy, and migraine containing, as an effective ingredient, a compound having the formula (I):

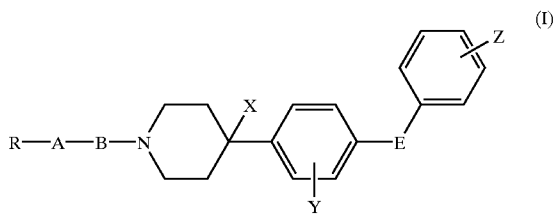

wherein, R is a hydrogen atom, an optionally substituted phenyl group, an optionally substituted phenoxy group, or an optionally substituted benzoyl group, A is a connecting bond, a cycloalkylene group, or an alkenylene group optionally substituted with a lower alkyl group, B is an alkylene group optionally substituted with a hydroxyl group or an alkoxy group or a group —NHCO(CH$_2$)$_n$—, where n is an integer of 1 to 5, E is a connecting bond, an oxygen atom, or a methylene group, X is a hydroxyl group or a hydrogen atom provided that, when E is an oxygen atom or a methylene group, X is not a hydrogen atom, and Y and Z may be the same or different from each other and represent a hydrogen atom, a halogen atom, an alkoxy group, or an alkyl group optionally substituted with a halogen atom or its pharmaceutically acceptable salt.

BEST MODE FOR CARRYING OUT THE INVENTION

The present inventors screened compounds by evaluating the inhibitory effects on the non-L-type $Ca^{2+}$ channel and $Na^+$ channel reported to be involved in the mechanism of cause of $Ca^{2+}$ overload [P. J. Pauwels et al.; Life Science, 48, 1881 (1991)]. As a result, it was found that the compounds having the formula (I) have a powerful action in suppressing one type of the non-L-type $Ca^{2+}$ channel, that is, the T-type $Ca^{2+}$ channel, and $Na^+$ channel and was effective in various types of animal disease models as well, whereby the present invention was completed.

In the present invention, as ischemic diseases, cerebral ischemic diseases, for example, cerebral infarction, intracerebral hemorrhage, transient ischemic attack, subarachnoid hemorrhage, head trauma, after effects of brain surgery, after effects of cerebral arteriosclerosis, and other functional and organic diseases of the brain, ischemic cardiac diseases, for example, variant angina, unstable angina, myocardial infarction, cardiovascular system disorders accompanying surgery for revascularization by PTCA/PTCR/CABG etc., malignant arrhythmia and other myocardial ischemia-reperfusion injury, and also disorders of transplanted organs at the time of organ transplants, and temporary blockage of the blood flow in organs at the time of surgery may be mentioned.

The compounds having the formula (I) according to the present invention include compounds having the formulas (Ia) and (Ib):

In the formula (Ia)

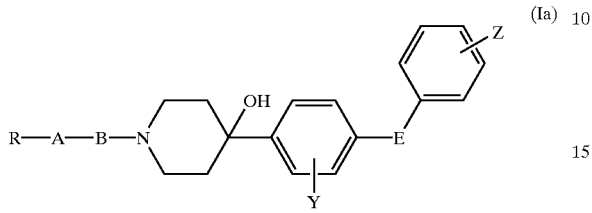

(Ia)

wherein, R, A, B, E, Y, and Z are as the same defined above, examples of the preferable substituent of the optionally substituted phenyl group, the optionally substituted phenoxy group, or the optionally substituted benzoyl group represented by R, include a halogen atom such as a fluorine atom, a chlorine atom, and a bromine atom, a hydroxyl group, a $C_1$ to $C_5$ optionally branched alkoxy group such as a methoxy group and an ethoxy group, and a $C_1$ to $C_5$ optionally branched alkyl group optionally substituted with a halogen atom such as a methyl group, an ethyl group and a trifluoromethyl group. Examples of the halogen atom of the $C_1$ to $C_5$ optionally branched alkyl group optionally substituted with a halogen atom include a fluorine atom, a chlorine atom, a bromine atom, etc.

Examples of the cycloalkylene group represented by A in formula (Ia) include preferably a $C_3$ to $C_6$ cycloalkylene group such as a 1,1-cyclopropylene group, a 1,2-cyclopropylene group, a 1,1-cyclobutylene group, a 1,1-cyclopentylene group, and a 1,1-cyclohexylene group, more preferably a 1,1-cyclopropylene group or a 1,2-cyclopropylene group. Preferable examples of the alkenylene group of the alkenylene group optionally substituted with a lower alkyl group include preferably a $C_2$ to $C_4$ alkenylene group such as a vinylene group and a butadiene group, more preferably a butadiene group. Examples of the alkyl groups of the alkenylene group optionally substituted with a lower alkyl group include a methyl group, an ethyl group, a propyl group, and an isopropyl group.

Preferable examples of the alkylene group of the alkylene group optionally substituted with a hydroxy group or an alkoxy group represented by B in formula (Ia) include preferably a $C_1$ to $C_6$ optionally branched alkylene group such as a methylene group, a dimethylene group, a trimethylene group, a tetramethylene group, a methylmethylene group, and a cyclopropylmethylene group, more preferably a methylene group, a dimethylene group, a trimethylene group, a tetramethylene group, and a cyclopropylmethylene group. Preferable examples of the alkoxy group of the alkylene group optionally substituted with an alkoxy group include a $C_1$ to $C_5$ optionally branched alkoxy group such as a methoxy group and an ethoxy group. Further, the integer n of 1 to 5 of the group —NHCO(CH$_2$)$_n$— is preferably 1 or 3.

Preferable examples of the halogen atom represented by Y or Z in formula (Ia) include a fluorine atom, a chlorine atom, and a bromine atom. Preferable examples of the alkoxy group include a $C_1$ to $C_5$ optionally branched alkoxy group such as a methoxy group and an ethoxy group. Preferable examples of the alkyl group optionally substituted with a halogen atom include a $C_1$ to $C_5$ optionally branched alkyl group such as a methyl group, an ethyl group, and a trifluoromethyl group. Examples of the halogen atom of an alkyl group optionally substituted with a halogen atom include a fluorine atom, a chlorine atom and a bromine atom.

In the formula (Ib)

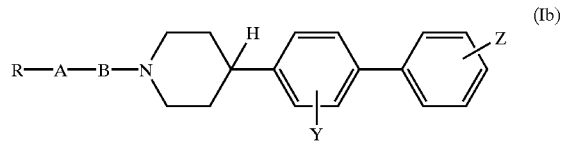

(Ib)

wherein, R, A, B, Y, and Z are the same as defined above, examples of the preferable substituent of the optionally substituted phenyl group, the optionally substituted phenoxy group, or the optionally substituted benzoyl group represented by R include a halogen atom such as a fluorine atom a chlorine atom and a bromine atom, a hydroxyl group, a $C_1$ to $C_5$ optionally branched alkoxy group such as a methoxy group and an ethoxy group, and a $C_1$ to $C_5$ optionally branched alkyl group optionally substituted with a halogen atom such as a methyl group, an ethyl group and a trifluoromethyl group. Examples of the halogen atom of the $C_1$ to $C_5$ optionally branched alkyl group optionally substituted with a halogen atom include a fluorine atom, a chlorine atom, a bromine atom, etc.

Examples of the cycloalkylene group represented by A in formula (Ib) include preferably a $C_3$ to $C_6$ cycloalkylene group such as a 1,1-cyclopropylene group, a 1,2-cyclopropylene group, a 1,1-cyclobutylene group, a 1,1-cyclopentylene group, and a 1,1-cyclohexylene group, more preferably a 1,1-cyclopropylene group and a 1,2-cyclopropylene group. Preferable examples of the alkenylene group of the alkenylene group optionally substituted with a lower alkyl group include preferably a $C_2$ to $C_4$ alkenylene group such as a vinylene group and a butadiene group, more preferably a butadiene group. Examples of the alkyl groups of the alkenylene group optionally substituted with a lower alkyl group include a methyl group, an ethyl group, a propyl group, and an isopropyl group.

Preferable examples of the alkylene group of the alkylene group optionally substituted with a hydroxy group or an alkoxy group represented by B in formula (Ib) include preferably a $C_1$ to $C_6$ optionally branched alkylene group such as a methylene group, a dimethylene group, a trimethylene group, a tetramethylene group, a methylmethylene group, and a cyclopropylmethylene group, particularly preferably a methylene group, a dimethylene group, a trimethylene group, a tetramethylene group, and a cyclopropylmethylene group. Preferable examples of the alkoxy group of the alkylene group optionally substituted with an alkoxy group include a $C_1$ to $C_5$ optionally branched alkoxy group such as a methoxy group and an ethoxy group. Further, the integer n of 1 to 5 of the group —NHCO(CH$_2$)$_n$— is preferably 1 or 3.

Preferable examples of the halogen atom represented by Y or Z include a fluorine atom, a chlorine atom and a bromine atom. Preferable examples of the alkoxy group include a $C_1$ to $C_5$ optionally branched alkoxy group such as a methoxy group and an ethoxy group. Preferable examples of the alkyl group optionally substituted with a halogen atom include a $C_1$ to $C_5$ optionally branched alkyl group such as a methyl group, an ethyl group and a trifluoromethyl group. Examples of the halogen atom of an alkyl group optionally substituted with a halogen atom include a fluorine atom, a chlorine atom and a bromine atom.

Among the compounds represented by the formula (I), particularly preferable examples are listed below:

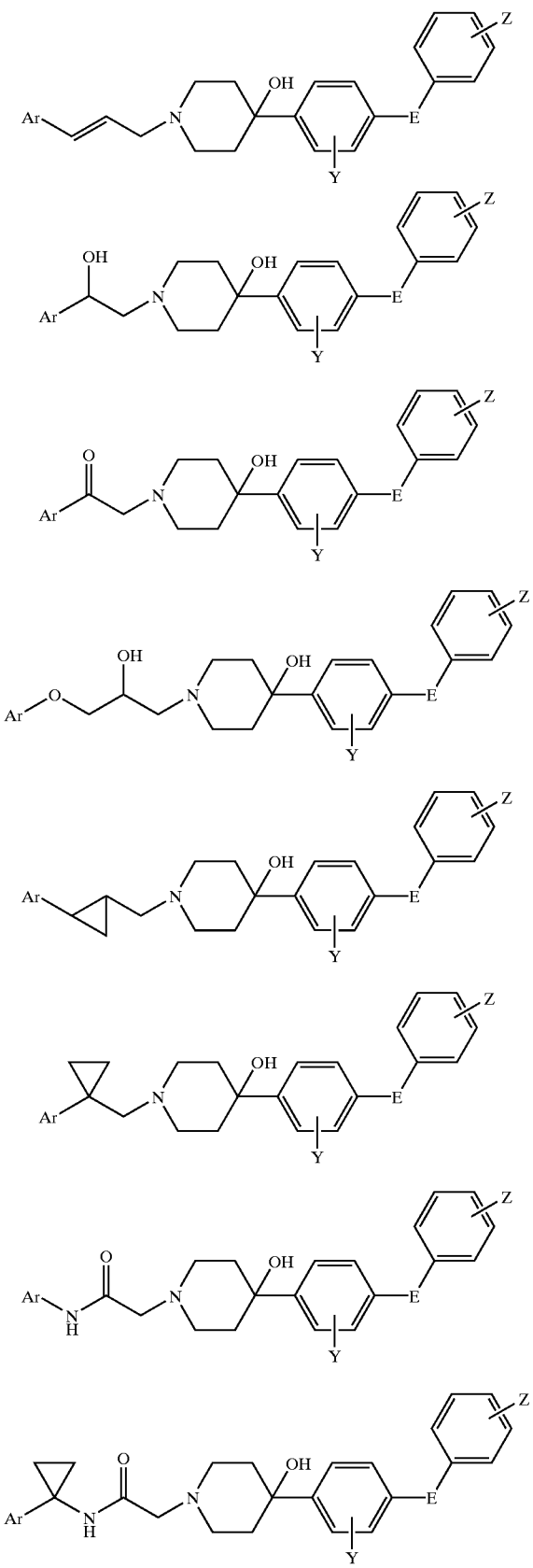

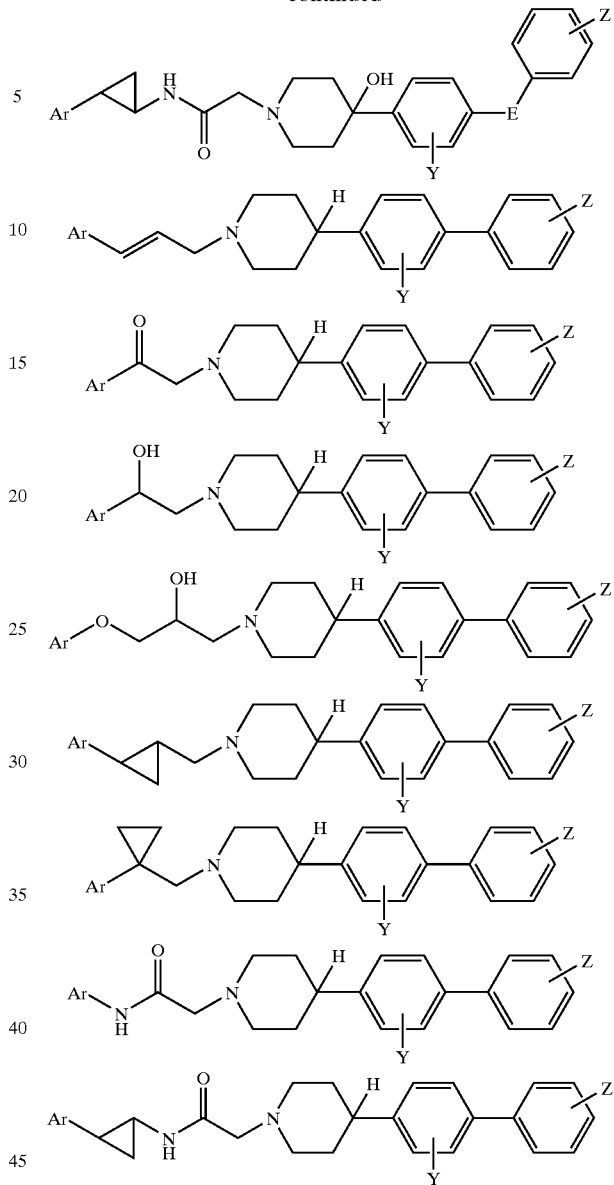

wherein, Ar represents an optionally substituted phenyl group and E, Y, and Z are the same as defined above.

Further, according to the present invention, there is provided a compound having the formula (I'):

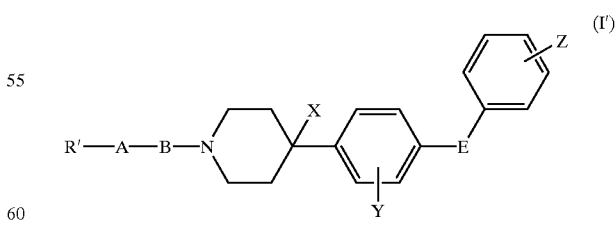

(I')

wherein, R' is an optionally substituted phenyl group, an optionally substituted phenoxy group, or an optionally substituted benzoyl group, A is a connecting bond, a cycloalkylene group, or an alkenylene group optionally substituted with a lower alkyl group, B is an alkylene group optionally substituted with a hydroxyl group or an alkoxyl group, or group —NHCO(CH$_2$)$_n$—, where n is an integer of 1 to 5, E is a connecting bond, an oxygen atom, or a methylene group, X is a hydroxyl group or a hydrogen atom provided that, when E is an oxygen atom or a methylene group, X is not a hydrogen atom, and Y and Z may be the same or different from each other and represent a hydrogen atom, a halogen atom, an alkoxy group, or an alkyl group optionally substituted with a halogen atom, provided that, when X is a hydrogen atom and R is an optionally substituted phenyl group or an optionally substituted phenoxy group, B is not an alkylene group, that, when X is a hydroxyl group and R is an optionally substituted phenoxy group, B is not an unsubstituted alkylene group, that, when X is a hydroxyl group, R is an optionally substituted phenyl group, and A is a connecting bond, B is not an unsubstituted alkylene group or group —NHCO(CH$_2$)$_n$—, and that, when X is a hydroxyl group, R is an optionally substituted phenyl group, and A is a cycloalkylene group, B is not a group —NHCO(CH$_2$)$_n$— and its pharmaceutically acceptable salt.

Examples of the preferable substituent of the optionally substituted phenyl group, the optionally substituted phenoxy group, or the optionally substituted benzoyl group represented by R' include a halogen atom such as a fluorine atom, a chlorine atom, and a bromine atom, a hydroxyl group, a C$_1$ to C$_5$ optionally branched alkoxy group such as a methoxy group and an ethoxy group, and a C$_1$ to C$_5$ optionally branched alkyl group optionally substituted with a halogen atom such as a methyl group, an ethyl group and a trifluoromethyl group. Examples of the halogen atom of the C$_1$ to C$_5$ optionally branched alkyl group optionally substituted with a halogen atom include a fluorine atom, a chlorine atom, a bromine atom, etc.

The preferable examples of the cycloalkylene group and the alkenylene group optionally substituted with a lower alkyl group represented by A, the preferable examples of the alkylene group optionally substituted with a hydroxyl group or an alkoxy group represented by B, the preferable examples of the integer n of the group —NHCO(CH$_2$)$_n$—, and the preferable examples of the halogen atom, an alkoxy group, or an alkyl group optionally substituted with a halogen atom represented by Y or Z are the same as the A, B, n, Y, and Z in the above formula (I).

Preferable examples of the compound of the formula (I') include compounds where, in the formula (I'), R', A, B, and X are selected from the group consisting of:

1) R' is an optionally substituted phenyl group, A is an alkenylene group optionally substituted with a lower alkyl group, B is an alkylene group optionally substituted with a hydroxyl group or an alkoxy group, or a group —NHCO(CH$_2$)$_n$—, where n is an integer of 1 to 5, and X is a hydroxyl group;

2) R' is an optionally substituted phenyl group, A is a connecting bond or a cycloalkylene group, B is an alkylene group substituted with a hydroxyl group, and X is a hydroxyl group;

3) R' is an optionally substituted phenyl group, A is a connecting bond or a cycloalkylene group, B is a group —NHCO(CH$_2$)$_n$—, where n is an integer of 1 to 5, and X is a hydroxyl group or a hydrogen atom;

4) R' is an optionally substituted phenoxy group, A is a connecting bond, a cycloalkylene group, or an alkenylene group optionally substituted with a lower alkyl group, B is an alkylene group substituted with a hydroxyl group, and X is a hydroxyl group; and 5) R' is an optionally substituted benzoyl group, A is a connecting bond, a cycloalkylene group, or an alkenylene group optionally substituted with a lower alkyl group, B is an alkylene group optionally substituted with a hydroxyl group or an alkoxy group or a group —NHCO(CH$_2$)$_n$—, where n is an integer of 1 to 5, and X is a hydroxyl group or a hydrogen atom and where further E is a connecting bond, an oxygen atom, or a methylene group, Y and Z may be the same or different from each other and represent a hydrogen atom, a halogen atom, an alkoxy group, or an alkyl group optionally substituted with a halogen atom.

The compounds having the formula (I') in the present invention include compounds having the formulas (I'a) and (I'b):

Formula (I'a)

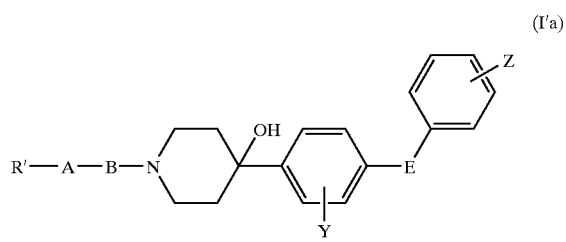

where, R', A, B, E, Y, and Z are the same as defined above;

Formula (I'b)

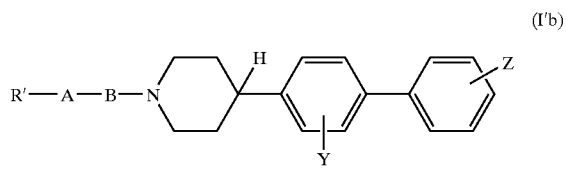

where, R', A, B, Y, and Z are the same as defined above.

The compounds having the formulas (I) and (I') include isomers. The present invention includes all of the individual isomers and mixtures thereof. For example, in the formulas (I) and (I'), when A is an alkenylene group optionally substituted with a lower alkyl group, there are two types of geometric isomers, that is, the (E)-form and (Z)-form, and when B is an alkylene group substituted with a hydroxyl group or an alkoxy group, there are a pair of optical isomers, and the compounds according to the present invention include individual isomers formed by all combinations of these and mixtures thereof.

In accordance with the present invention, there is further provided a compound having the formula (II):

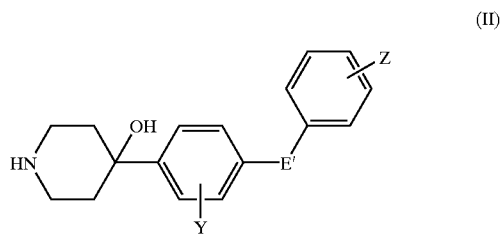

where, E' is an oxygen atom or a methylene group, and Y and Z may be the same or different from each other and represent a hydrogen atom, a halogen atom, an alkoxy group, or an alkyl group optionally substituted with a halogen atom.

The compounds having the formulas (I) and (I') according to the present invention may be synthesized in, for example, the following manners. These methods will be successively explained below.

The compounds (Ia) and (I'a) where, in the formulas (I) and (I'), X is a hydroxyl group, can be obtained as follows: That is, the compound (IV) is obtained from a known starting substance (III) (step 1), then is converted to the compound (IIa) (step 2), which is then allowed to react with the compound (V) or (V') to obtain the compound (Ia) or (I'a) (step 3). The compounds (Ia) and (I'a) where B is an alkylene group substituted with a hydroxyl group are obtained from the compound (IIa) and compound (VI) or (VI') (step 4). The compounds (Ib) and (I'b) where, in the formula (I), E is a connecting bond and X is a hydrogen atom are obtained by a reaction of the compound (IIb), derived from the compound (IV') (step 5), with the compound (V) or (V') (step 6). The compounds (Ib) and (I'b) where B is an alkylene group substituted with a hydroxyl group are obtained from the compound (IIb) and the compound (VI) or (VI') (step 7).

Step 1

The compound(IV) may be synthesized from the known starting substance (III) by the following method:

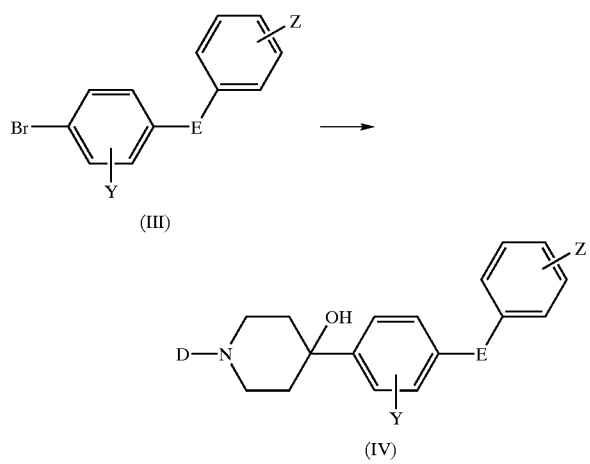

wherein, E, Y, and Z are the same as defined above, and D represents a benzyl group, a p-methoxybenzyl group, a tert-butoxycarbonyl group, an ethoxycarbonyl group, or an acetyl group.

That is, an aryl bromide derivative (III) is converted to a corresponding aryl Grignard reagent or aryl lithium reagent by the conventional method, then is allowed to react in tetrahydrofuran, diethylether, ethyleneglycol dimethylether, toluene, or another solvent not participating in the reaction at −100 to 50° C., preferably −78° C. to room temperature, with 1 to 1.5 equivalents of the known starting material N-benzyl-4-piperidone, N-(p-methoxybenzyl)-4-piperidone, N-tert-butoxycarbonyl-4-piperidone, N-ethoxycarbonyl-4-piperidone, or N-acetyl-4-piperidone for 1 to 6 hours so as to obtain the compound having the formula (IV).

The starting material (III) used in the reaction is a known compound or can be synthesized by a known method [L. Martin et al., J. Med. Chem., 22, 1347 (1979); J. -P. Genet et al., Tetrahedron Lett., 37, 3857 (1996); G. Faye Crr et al., J. Med. Chem., 40, 1179 (1997)]. For example, 4-bromodiphenylether, 4-bromophenylether, 4-bromo-4'-fluorodiphenylether, 4-bromo-3'-fluorodiphenylether, 4-bromo-2'-fluorodiphenylether, 3-bromo-4'-fluorodiphenyl-ether, 3-bromo-3'-fluorodiphenylether, 3-bromo-2'-fluorodiphenylether, 2-bromo-4'-fluorodiphenylether, 2-bromo-3'-fluorodiphenylether, 2-bromo-2'-fluorodiphenyl-ether, 2-bromodiphenylmethane, 3-bromodiphenylmethane, 4-bromodiphenylmethane, 2-bromo-4'-fluorodiphenylmethane, 3-bromo-4'-fluorodiphenylmethane, 4-bromo-4'-fluoro-diphenylmethane, 2-bromo-4'-chlorodiphenylmethane, 3-bromo-4'-chlorodiphenylmethane, 4-bromo-4'-chloro-diphenylmethane, 2-bromo-4'-methoxydiphenylmethane, 3-bromo-4'-methoxydiphenylmethane, 4-bromo-4'-methoxydiphenylmethane, 2-bromo-4'-trifluoromethyl-diphenylmethane, 3-bromo-4'-trifluoromethyldiphenyl-methane, 4-bromo-4'-trifluoromethyldiphenylmethane, 3-bromo-4-fluorodiphenylmethane, 3-bromo-4,4'-difluorodiphenylmethane, 3-bromo-4-fluoro-4'-chlorodiphenylmethane, 3-bromo-4-fluoro-4'-methoxydiphenylmethane, 3-bromo-4'-fluoro-4'-trifluoromethyldiphenylmethane, 3-bromo-4-methoxydiphenylmethane, 3-bromo-4-methoxy-4'-fluorodiphenylmethane, 3-bromo-4-methoxy-4'-chloro-diphenylmethane, 3-bromo-4,4'-dimethoxydiphenylmethane, 3-bromo-4-methoxy-4'-trifluoromethyldiphenylmethane, 5-bromo-2-methoxydiphenylmethane, 5-bromo-2-methoxy-4'-fluorodiphenylmethane, 5-bromo-2-methoxy-4'-chloro-diphenylmethane, 5-bromo-2,4'-dimethoxydiphenylmethane, 5-bromo-2-methoxy-4'-trifluoromethyldiphenylmethane, 4-bromobiphenyl, 4-bromo-2-fluorobiphenyl, 4-bromo-4'-fluorobiphenyl, 4-bromo-4'-methoxybiphenyl, 4-bromo-4'-methylbiphenyl, 4-bromo-4'-trifluoromethylbiphenyl, 4,4'-dibromobiphenyl, etc. can be used. Further, as the conditions for preparing the Grignard reagent and the organolithium reagent, the various methods described in the "Compendium for Organic Synthesis" (Wiley-Interscience: A Division of John Wiley & Sons Ltd.) etc. can be used.

The compound obtained from the above reaction can be used as is for the next step or, if necessary, can be used after purification by a conventional method such as recrystallization or column chromatography.

Step 2

The compound (IIa) can be synthesized from the compound (IV) obtained in step 1:

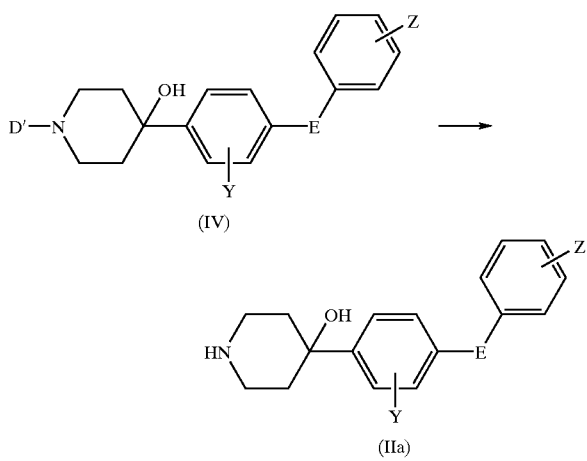

where, E, Y, and Z are the same as defined above, and D' is a benzyl group or a p-methoxybenzyl group.

The compound (IV) obtained in step 1 can be converted to the compound having the formula (IIa) by hydrogenation in ethyl acetate, methanol, ethanol, isopropyl alcohol, or another solvent not participating in the reaction in the presence of a catalytic amount of palladium carbon, palladium hydroxide, platinum, etc. at atmospheric pressure to 6 atmospheres. Further, in the reaction, acetic acid, hydrochloric acid, or other acid may be added, if necessary.

Step 3

The compounds (Ia) and (I'a) where X is a hydroxyl group in the formulas (I) and (I') can be synthesized by a reaction of the compound (V) or (V') with the compound (IIa) obtained in step 2.

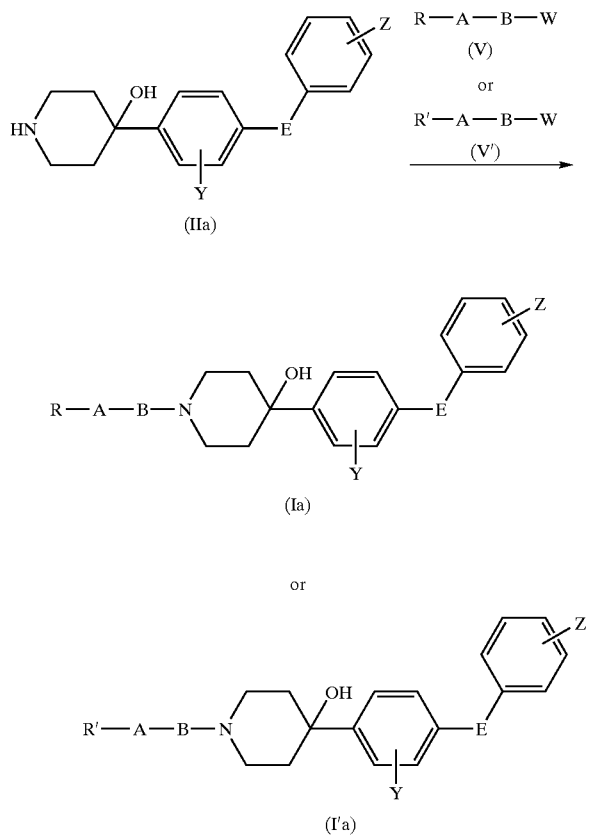

where, R, R', A, B, E, Y, and Z are the same as defined above, and W is a group which can be easily exchanged with an amino group.

That is, the compound (IIa) obtained in step 2 is heated and stirred in benzene, toluene, tetrahydrofuran, dioxane, dimethylformamide, dimethylsulfoxide, acetonitrile, acetone, or another solvent not participating in the reaction, in the presence of triethylamine, diisopropylethylamine, pyridine, or another organic base or sodium carbonate, potassium carbonate, cesium carbonate, cesium fluoride, sodium hydrogencarbonate, potassium hydrogencarbonate, or another inorganic base, at room temperature to 150° C., preferably room temperature to 100° C., with 1.0 to.1.5 equivalents of the compound (V) or (V') to obtain the compound having the formula (Ia) or (I'a). Further, in this reaction, if necessary, sodium iodide or tetrabutylammonium iodide may be added. W is a leaving group easily exchanged with an amino group. For example, a chlorine atom, a bromine atom, or other halogen atom, an alkylsulfonyloxy group such as a methanesulfonyloxy group, or an arylsulfonyloxy group such as a p-toluenesulfonyloxy group may be mentioned.

As the compound (V) or (V') used in this reaction, a commercially available or known compound or one which can be synthesized by a known method can be used. For example, methyl iodide, ethyl iodide, ethyl bromide, propyl bromide, cinnamyl bromide, 3-bromo-2-methyl-1-phenyl-1-propene, 4-fluorocinnamyl bromide, (2,3,4-trimethoxy) cinnamyl bromide, 1-bromo-3-phenylpropene, (1-bromoethyl)benzene, (2-bromoethyl)benzene, 4-methoxycinnamyl bromide, 2-(4-fluorophenyl)oxyethyl bromide, 2-phenyloxyethyl bromide, 4-(4-fluorophenyl) oxybutyl bromide, 4-phenyloxybutyl bromide, 2-phenyloxypropyl bromide, trans-(2-phenyl) cyclopropylmethyl bromide, 1-phenyl-1-cyclopropylmethyl bromide, 1-phenyl-1-cyclopropanemethyl bromide, 1-phenyl-1-cyclopentanemethyl bromide, phenacyl bromide, 2-bromo-4'-methoxyacetophenone, 2-bromo-4'-fluoroacetophenone, 2-bromo-4'-chloroacetophenone, 2-bromopropiophenone, 2-bromo-2'4'-dimethoxyacetophenone, 2-bromo-2'5'-dimethoxyacetophenone, 2-bromo-4'-methylacetophenone, 4-chlorobutyrophenone, 4-chloro-4,-fluorobutyrophenone, 2-bromomethyl-2-phenyl-1,3-dioxolane, 2-bromomethyl-2-(4-fluorophenyl)-1,3-dioxolane, 2-bromomethyl-2-(4-chlorophenyl)-1,3-dioxolane, 2-bromomethyl-2-(4-methoxyphenyl)-1,3-dioxolane, 2-(1-bromoethyl)-2-phenyl-1,3-dioxolane, 2-bromomethyl-2-(4-methylphenyl)-1,3-dioxolane, 2-bromomethyl-2-(2,4-dimethoxyphenyl)-1,3-dioxolane, 2-bromomethyl-2-(2,5-dimethoxyphenyl)-1,3-dioxolane, 2,3,4-trimethoxybenzyl chloride, benzyl bromide, 4-fluorobenzyl bromide, 2-fluorobenzyl bromide, 3-fluorobenzyl bromide, 4-(trifluoromethyl)benzyl bromide, 2-(trifluoromethyl)benzyl bromide, 3-(trifluoromethyl) benzyl bromide, 2-bromo-1-indanone, 2-bromomethylbenzofuran, (2-bromo-1-hydroxyiminoethyl) benzene, 3-methoxybenzyl chloride, 4-methoxybenzyl chloride, cinnamyl chloride, (2-bromo-1-methoxyethyl)benzene, 1-(4-chlorophenyl) cyclobutanemethyl bromide, 1-(4-chlorophenyl) cyclopentanemethyl bromide, 1-(4-methoxyphenyl) cyclopentanemethyl bromide, (2-bromo-1,1-diethoxyethyl) benzene, N-(2,6-dimethylphenyl)-2-bromoacetamide, 2-bromo-N-(trans-2-phenylcyclopropyl) acetamide, N-(1-phenyl)cyclopropyl-2-bromoacetamide, N-(2,6-dimethylphenyl)-4-bromobutylamide, N-(2,4,6-trimethylphenyl)-4-bromobutylamide, N-phenyl-2-bromoacetamide, N-(2,6-diisoopropylphenyl)-2-bromoacetamide, N-(1-phenyl)cyclopropyl-2-bromoacetamide, etc. can be used.

Further, the compound where in the formula (I'a) R' is an optionally substituted phenyl group, A is a connecting bond, and B is an alkylene group substituted with a hydroxyl group can be also synthesized by a reduction of the compound (I'a) obtained in this step where R' is an optionally substituted benzoyl group, A is a connecting bond, and B is an alkylene group by a conventional method.

Step 4

The compound (Ia') or (I'a') where A is a bond arm and B is an alkylene group substituted with a hydroxyl group in the formulas (Ia) and (I'a) can be synthesized from the compound (IIa) obtained in step 2:

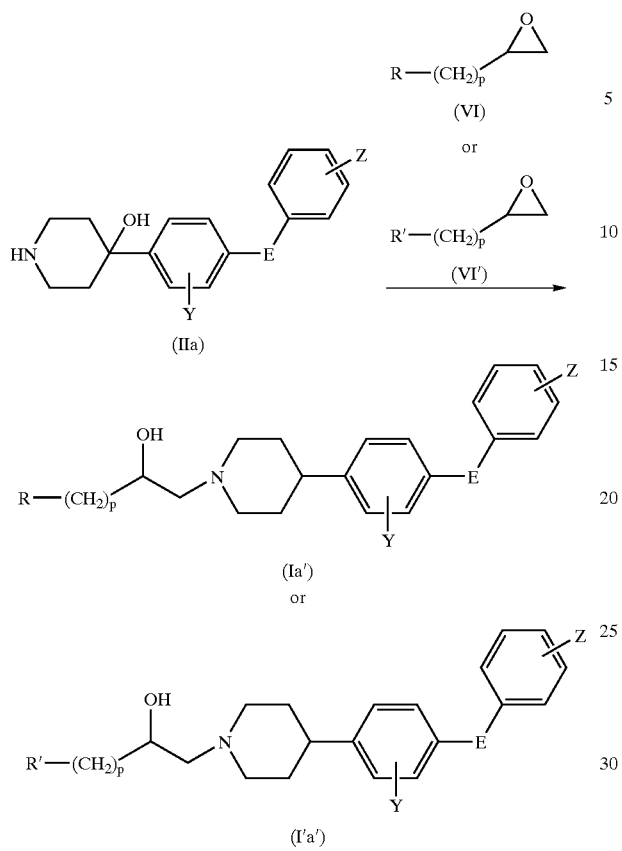

(VI)

(IIa)

(VI')

(Ia')

or (I'a')

where, R, R', E, Y, and Z are the same as defined above, and p is 0 or an integer of 1.

That is, it can be synthesized by a reaction of the compound (IIa) obtained in step 2 in a solvent not participating in the reaction, such as benzene, toluene, tetrahydrofuran, diethyl ether, ethyleneglycol dimethyl ether, dioxane, dimethylformamide, dimethylsulfoxide, acetonitrile, methanol, ethanol, isopropyl alcohol, tert-butyl alcohol, ethylene glycol, at room temperature to 200° C., preferably 50 to 150° C., with 0.9 to 1.5 equivalents of the compound (VI) or (VI') for 1 to 24 hours.

As the compound (VI) or (VI') used in this reaction, a commercially available or known compound or one which can be synthesized by a known method can be used. For example, 1,2-epoxyethylbenzene, (R)-(+)-1,2-epoxyethylbenzene, (S)-(−)-1,2-epoxyethylbenzene, (1R, 2R)-(+)-1-phenylpropylene oxide, (1S, 2S)-(−)-1-phenylpropylene oxide, 1,2-epoxy-3-phenoxypropane, (R)-(−)-2-(benzyloxymethyl)oxirane, (S)-(+)-2-(benzyloxymethyl)oxirane, 2,3-epoxypropylbenzene, glycidyl 2-methylphenyl ether, 4-tert-butylphenyl-2,3-epoxypropyl ether, 4-chlorophenyl-2,3-epoxypropyl ether, 2,3-epoxypropyl-4-methoxyphenyl ether, (R)-(−)-1,2-epoxy-3-phenoxypropane, (S)-(+)-1,2-epoxy-3-phenoxypropane, etc. may be used.

Further, in this reaction, if necessary, one or a combination of a plurality of organic base such as triethylamine, diisopropylethylamine and pyridine, inorganic base such as sodium carbonate, potassium carbonate, cesium carbonate, cesium fluoride, sodium hydrogencarbonate and potassium hydrogencarbonate, or metal salt such as sodium iodide, tetrabutylammonium iodide, lithium carbonate, lithium chloride, zinc bromide and magnesium bromide may be added.

Step 5

The compound (IIb) can be synthesized from the compound (IV') where E is a connecting bond among the compounds represented by the formula (IV) obtained in step 1.

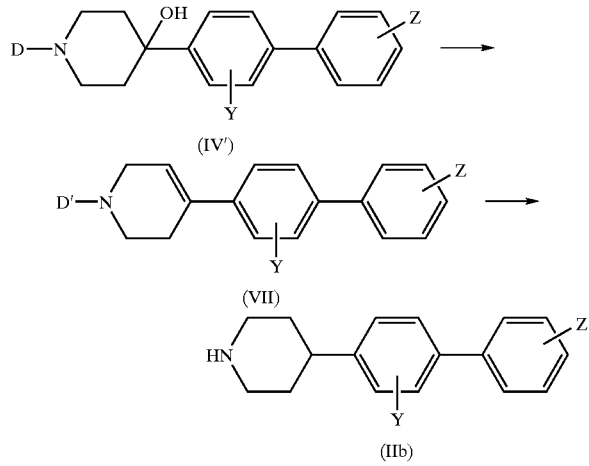

(IV')

(VII)

(IIb)

where, Y, Z, D, and D' are the same as defined above.

The compound (IV') obtained in step 1 is treated under non-solvent conditions or in solvent not participating in the reaction such as tetrahydrofuran, diethyl ether, ethyleneglycol dimethylether, benzene, toluene, methylene chloride, chloroform, carbon tetrachloride, water, methanol and ethanol, at −20 to 150° C., preferably 0 to 80° C., with 1 to 20 equivalents of acetic acid, trifluoroacetic acid, methanesulfonic acid, trifluoromethanesulfonic acid, and other organic acids or hydrochloric acid, sulfuric acid, nitric acid, or other inorganic acids for 1 to 12 hours, or the compound (IV') is reacted in solvent not participating in the reaction such as benzene, toluene, methylene chloride, chloroform, and carbon tetrachloride, if necessary, in the presence of triethylamine, pyridine, diisopropylethylamine, or other bases, at −20 to 150° C., preferably 0 to 100° C., with 1 to 5 equivalents of thionyl chloride, methanesulfonylchloride, trifluoromethanesulfonyl chloride, trifluoromethanesulfonic anhydride, p-toluene sulfonyl chloride, phosphorus oxychloride, or other acid chloride derivatives for 1 to 6 hours, and the subsequent acid treatment similar to the above, so as to obtain a compound having the formula (VII). Next, the compound (VII) is treated by a similar method as described in step 2 to obtain the compound of the formula (IIb).

The compounds obtained by the above reactions can be used, as they are, for the next step, but can also be used after purification if necessary by a conventional method such as recrystallization or column chromatography.

Step 6

The compound (Ib) or (I'b) where X is a hydrogen atom in the formula (I) or (I') can be synthesized by a similar method as described in step 3 from the compound (IIb) obtained in step 5 and the compound (V) or (V'):

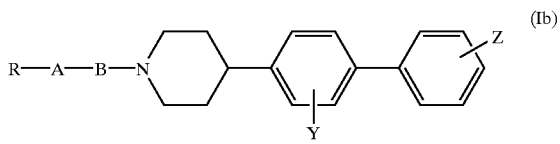

(Ib)

-continued

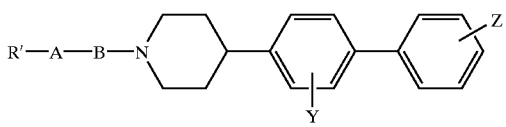
(I'b)

where, R, R', A, B, Y, and Z are the same as defined above.

Step 7

Among the compounds represented by the formulas (Ib) and (I'b), the compound (Ib') or (I'b') where A is a connecting bond and B is an alkylene group substituted with a hydroxyl group can be synthesized by a similar method as described in step 4 from the compound (IIb) obtained in step 5:

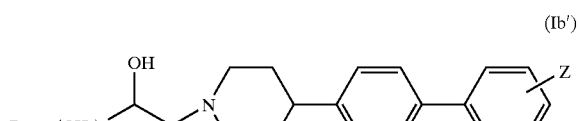
(Ib')

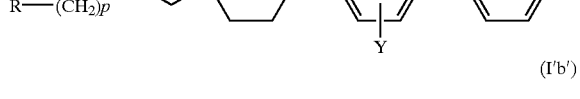
(I'b')

where, R, R', Y, Z, and p are the same as defined above.

The isomers included in the compound having the formulas (I) and (I') of the present invention may be separated by conventional methods, for example, recrystallization, column chromatography, thin layer chromatography, high pressure liquid chromatography, or similar methods using optically active reagents.

The compound having the formulas (I) or (I') of the present invention may be dissolved in a suitable organic solvent, for example, ether, tetrahydrofuran, methylene chloride, chloroform, benzene, toluene, etc. and treated with an inorganic or organic acid to obtain the corresponding salt. Examples of the inorganic acid used here include hydrochloric acid, sulfuric acid, nitric acid, phosphoric acid, periodic acid, etc. and examples of the organic acid include formic acid, acetic acid, butyric acid, oxalic acid, malonic acid, propionic acid, valeric acid, succinic acid, fumaric acid, maleic acid, tartaric acid, citric acid, malic acid, benzoic acid, p-toluenesulfonic acid, methanesulfonic acid, etc.

The compound according to the present invention is low in toxicity. For example, the 50% lethal dosage $LD_{50}$ of acute toxicity of the compound of Compound No. 17, calculated from the death rate up to 24 hours after intravenous injection of the drug into ddY mice (male, 6 weeks old) by a conventional method, was 32 mg/kg.

The compound having the formula (I) or (I') of the present invention is low in toxicity and can be used alone by itself, or if desired, can be prepared with other normal pharmaceutically allowable known and generally used carriers into preparations designed for the alleviation and treatment of symptoms due to ischemic diseases. For example, the effective ingredient can be administered orally or nonorally by itself or made into a capsule, tablet, injection, or other suitable preparation together with usually used excipients.

For example, capsule preparations are prepared by mixing the original powder with lactose, starch or its derivatives, cellulose derivatives or other excipients and packing the mixture into gelatin capsules. Further, tablets can be prepared by adding and kneading in, in addition to said excipient, sodium carboxymethylcellulose, alginic acid, arabia gum, and other binders and water, if necessary granulating the same, then further adding talc, stearic acid, or other lubricants and preparing the final form using a usual compression tablet-making machine. At the time of non-oral administration using injection, the effective ingredient is dissolved together with a solubilizer in sterilized distilled water or sterilized physiological saline and sealed in an ampule to make the injection preparation. If necessary, a stabilizing agent, buffer, etc. may also be included.

The dosage of the pharmaceutical composition for the alleviation or treatment of ischemic diseases differs depending on various factors, for example, the symptoms, gravity of symptoms, age, and complications of the patient to be treated and depending on the route of administration, the form of the preparation, the frequency of administration, etc., but usually is 0.1 to 1000 mg/day/person, preferably 1 to 500 mg/day/person as an effective ingredient in the case of oral administration, and 1/100 to ½ the amount of oral dosage in the case of non-oral administration. These amounts of dosages may be suitably changed in accordance with the age, symptoms, etc. of the patient.

EXAMPLES

The present invention will now be explained in further detail with reference to the follows Reference Examples and Examples, but the present invention is of course not limited in scope to these Examples.

Example 1

Synthesis of N-benzyl-4-(3-fluoro-4-phenyl)phenyl-4-piperidinol (1) (Note: Compound No. 1 of Table 1 (Same Below))

To a 15 ml of tetrahydrofuran solution of 3 g of N-benzyl-4-piperidone, 32 ml of (3-fluoro-4-phenyl)phenyl magnesium bromide (0.6 mol/liter tetrahydrofuran solution) prepared from 4-bromo-2-fluorobiphenyl is added dropwise under ice cooling and stirred for 1 hour. To the reaction mixture, a 30 ml of saturated aqueous solution of ammonium chloride was added and extraction performed by ether. The extract was washed with saturated saline, dried, filtered, then concentrated under reduced pressure to obtain a residue which was then purified by silica gel column chromatography (chloroform:methanol=20:1) to obtain 3.56 g of the above-referenced compound (1) (yield 62%).

Example 2

Synthesis of N-benzyl-4-(4-phenyl)phenyl-4-piperidinol (2)

The same procedure was followed as in Example 1 using 4-bromobiphenyl to produce the above.

Example 3

Synthesis of N-benzyl-4-(4-phenoxy)phenyl-4-piperidinol (3)

The same procedure was followed as in Example 1 using 4-bromodiphenyl ether to produce the above.

Example 4

Synthesis of N-benzyl-4-[4-(4-fluorophenyl)methylphenyl]-4-piperidinol (4)

To a 12 ml of ether solution of 1.4 g of 4-bromo-4'-fluorodiphenylmethane, 3.6 ml of n-butyl lithium (1.6 mol/ liter hexane solution) was added dropwise at −78° C. The mixture was warmed up to −20° C. and stirred for 1 hour, then a 5 ml of ether solution of 1 g of N-benzyl-4-piperidone was added dropwise. The mixture was stirred at 0° C. for 3 hours, then 10 ml of saturated aqueous solution of ammonium chloride was added and extracted with ether. The extract was washed with saturated saline, dried, filtered, then concentrated under reduced pressure to obtain a residue which was then purified by silica gel column chromatography (chloroform:methanol=10:1) to obtain 1.03 g of the above-referenced compound (4) (yield 52%).

Example 5

Synthesis of N-benzyl-4-[4-(4-fluoro)phenoxy]phenyl-4-piperidinol (5)

The same procedure was followed as in Example 1 using 4-bromo-4'-fluorodiphenyl ether to produce the above.

Reference Example 1

Synthesis of N-tert-butoxycarbonyl-4-(3-fluoro-4-phenyl)phenyl-4-piperidinol (6)

The same procedure was followed as in Example 1 using N-tert-butoxycarbonyl-4-piperidone and 4-bromo-2-fluorobiphenyl to produce the above.

Reference Example 2

Synthesis of N-tert-butoxycarbonyl-4-(4-phenyl)phenyl-4-piperidinol (7)

The same procedure was followed as in Example 1 using N-tert-butoxycarbonyl-4-piperidone and 4-bromobiphenyl to produce the above.

Reference Example 3

Synthesis of 4-(3-fluoro-4-phenyl)phenyl-1,2,3,6-tetrahydropyridine (8)

To a 10 ml of methylene chloride solution of 1.76 g of the compound (6) synthesized in Reference Example 1, 30 ml of trifluoroacetic acid was added drop-wise under ice cooling. The mixture was stirred at room temperature overnight, then was adjusted to pH 9 to 10 by a 10% aqueous solution of sodium hydroxide and extracted with ether. The extract was dried, filtered, then concentrated under reduced pressure to obtain a residue which was purified by silica gel column chromatography (chloroform:methanol=10:1) to obtain 855 mg of the above-referenced compound (8) (yield 71%).

Reference Example 4

Synthesis of 4-(3-fluoro-4-phenyl)phenylpiperidine (9)

To a 100 ml of methanol solution of 855 mg of the compound (8) synthesized in Reference Example 3, 130 mg of palladium carbon and 0.5 ml of acetic acid were added and then hydrogenated under atmospheric pressure at room temperature. After the end of the reaction, the insolubles were filtered off and the filtrate was concentrated under reduced pressure. The residue obtained was then purified by silica gel column chromatography (methylene chloride:methanol=10:1) to obtain 782 mg of the above-referenced compound (9) (yield 91%).

Reference Example 5

Synthesis of 4-(4-phenyl)phenyl-1,2,3,6-tetrahydropyridine (10)

The same procedure was followed as in Reference Example 3 to produce the above compound from the compound (7) synthesized in Reference Example 2.

Reference Example 6

Synthesis of 4-(4-phenyl)phenylpyridine (11)

The same procedure was followed as in Reference Example 4 to produce the above compound from the compound (10) synthesized in Reference Example 5.

Example 6

Synthesis of 4-(3-fluoro-4-phenyl)phenyl-4-piperidinol (12)

To a 50 ml of methanol solution of 1.39 g of the compound (1) synthesized in Example 1, 280 mg of palladium hydroxide was added. The mixture was hydrogenated at room temperature under 5 atmospheres. After the end of the reaction, the insolubles were filtered off and the filtrate was concentrate under reduced pressure. The obtained residue was then purified by silica gel column chromatography (methylene chloride:methanol=10:1) to obtain 710 mg of the above-referenced compound (12) (yield 68%).

Example 7

Synthesis of 4-(4-phenyl)phenyl-4-piperidinol (13)

The same procedure was followed as in Example 6 to produce the above compound from the compound (2) synthesized in Example 2.

Example 8

Synthesis of 4-(4-phenoxy)phenyl-4-piperidinol (14)

The same procedure was followed as in Example 6 to produce the above compound from the compound (3) synthesized in Example 3.

Example 9

Synthesis of 4-[4-(4-fluorophenyl)methylphenyl]-4-piperidinol (15)

The same procedure was followed as in Example 6 to produce the above compound from the compound (4) synthesized in Example 4.

Example 10

Synthesis of 4-[4-(4-fluoro)phenoxy]phenyl-4-piperidinol (16)

The same procedure was followed as in Example 6 to produce the above compound from the compound (5) synthesized in Example 5.

Example 11

Synthesis of (E)-4-(3-fluoro-4-phenyl)phenyl-1-(3-phenyl-2-propenyl)-4-piperidinol (17)

To an 8 ml of acetonitrile solution of 300 mg of the compound (12) synthesized in Example 6, 220 mg of cinnamyl bromide and 0.4 ml of triethylamine were added and the mixture heated at reflux for 2 hours. To the reaction mixture, 10 ml of ice water was added and extracted with ethyl acetate. The extract was dried, filtered, then concentrated under reduced pressure to obtain a residue which was then purified by silica gel column chromatography (methylene chloride:methanol=25:1) to obtain 302 mg of the above-referenced compound (17) (yield 72%).

Example 12

Synthesis of (E)-4-(3-fluoro-4-phenyl)phenyl-1-(3-phenyl-2-propenyl)piperidine (18)

The same procedure was followed as in Example 11 to produce the above compound from the compound (9) synthesized in Reference Example 4.

Example 13

Synthesis of 4-(3-fluoro-4-phenyl)phenyl-1-(2-phenyl-2-oxoethyl)piperidine (19)

The same procedure was followed as-in Example 11 to produce the above compound from the compound (9) synthesized in Reference Example 4 and phenacyl bromide.

Example 14

Synthesis of 4-(3-fluoro-4-phenyl)phenyl-1-(2-phenyl-2-oxoethyl)-4-piperidinol (20)

The same procedure was followed as in Example 11 to produce the above compound from the compound (12) synthesized in Example 6 and phenacyl bromide.

Example 15

Synthesis of 4-(3-fluoro-4-phenyl)phenyl-1-[2-(4-methoxyphenyl)-2-oxoethyl]-4-piperidinol (21)

The same procedure was followed as in Example 11 to produce the above compound from the compound (12) synthesized in Example 6 and 2-bromo-4'-methoxyacetophenone.

Example 16

Synthesis of (E)-4-(4-phenyl)phenyl-1-(3-phenyl-2-propenyl)piperidine (22)

The same procedure was followed as in Example 11 to produce the above compound from the compound (11) synthesized in Reference Example 6.

Example 17

Synthesis of 4-(4-phenyl)phenyl-1-(2-phenyl-2-oxoethyl)piperidine (23)

The same procedure was followed as in Example 11 to produce the above compound from the compound (11) synthesized in Reference Example 6 and phenacyl bromide.

Example 18

Synthesis of 4-(3-fluoro-4-phenyl)phenyl-1-(2-hydroxy-3-phenoxy)propyl-4-piperidinol (24)

A mixture of 300 mg of the compound (12) synthesized in Example 6 and 160 mg of phenyl glycidyl ether in an 8 ml of isopropyl alcohol were stirred at 100° C. for 2 hours. The reaction mixture was concentrated under reduced pressure to obtain a residue which was then purified by silica gel column chromatography (chloroform:methanol=40:1) to obtain 420 mg of the above-referenced compound (24) (yield 96%).

Example 19

Synthesis of 4-(3-fluoro-4-phenyl)phenyl-1-(trans-2-phenyl-1-cyclopropylmethyl)piperidine (25)

The same procedure was followed as in Example 11 to produce the above compound from the compound (9) synthesized in Reference Example 4 and trans-2-phenyl-1-cyclopropylmethyl bromide.

Example 20

Synthesis of 4-(3-fluoro-4-phenyl)phenyl-1-(1-phenyl-1-cyclopropane)methyl-1-piperidinol (26)

The same procedure was followed as in Example 11 to produce the above compound from the compound (12) synthesized in Example 6 and 1-phenyl-1-cyclopropanemethyl bromide.

Example 21

Synthesis of 4-(4-phenyl)phenyl-1-(trans-2-phenyl-1-cyclopropylmethyl)piperidine (27)

The same procedure was followed as in Example 11 to produce the above compound from the compound (11) synthesized in Reference Example 6 and trans-2-phenyl-1-cyclopropylmethyl bromide.

Example 22

Synthesis of 4-(4-phenyl)phenyl-1-(1-phenyl-1-cyclopropane)methylpiperidine (28)

The same procedure was followed as in Example 11 to produce the above compound from the compound (11) synthesized in Reference Example 6 and 1-phenyl-1-cyclopropanemethyl bromide.

Example 23

Synthesis of 4-(4-phenyl)phenyl-1-(2-hydroxy-3-phenoxy)propylpiperidine (29)

The same procedure was followed as in Example 18 to produce the above compound from the compound (11) synthesized in Reference Example 6.

Example 24

Synthesis of N-(2,6-dimethylphenyl)-4-(3-fluoro-4-phenyl)phenyl-1-piperidinacetamide (30)

The same procedure was followed as in Example 11 to produce the above compound from the compound (9) synthesized in Reference Example 4 and N-(2,6-dimethylphenyl)-2-bromoacetamide [I. Mezo et al., J. Label, Compounds, 8, 359 (1972)],:

Example 25

Synthesis of N-(trans-2-phenyl-1-cyclopropyl)-4-(3-fluoro-4-phenyl)phenyl-1-piperidinacetamide (31)

The same procedure was followed as in Example 11 to produce the above compound from the compound (9) synthesized in Reference Example 4 and 2-bromo-N-(trans-2-phenylcyclopropyl)acetamide [N. Bodor et al., J. Pharm. Sci., 80, 255 (1991)].

Example 26

Synthesis of 4-(4-phenyl)phenyl-1-(trans-2-phenyl-1-cyclopropylmethyl)-4-piperidinol (32)

The same procedure was followed as in Example 11 to produce the above compound from the compound (12) synthesized in Example 6 and trans-2-phenyl-1-cyclopropylmethyl bromide.

Example 27

Synthesis of (E)-4-(4-phenyl)phenyl-1-(3-phenyl-2-propenyl)-4-piperidinol (33)

The same procedure was followed as in Example 11 to produce the above compound from the compound (13) synthesized in Example 7.

Example 28

Synthesis of (E)-4-(4-phenoxy)phenyl-1-(3-phenyl-2-propenyl)-4-piperidinol (34)

The same procedure was followed as in Example 11 to produce the above compound from the compound (14) synthesized in Example 8.

Example 29

Synthesis of 4-(4-phenoxy)phenyl-1-(2-phenyl-2-oxoethyl)-4-piperidinol (35)

The same procedure was followed as in Example 11 to produce the above compound from the compound (14) synthesized in Example 8 and phenacyl bromide.

Example 30

Synthesis of 4-(4-phenoxy)phenyl-1-(2-hydroxy-3-phenoxy)propyl-4-piperidinol (36)

The same procedure was followed as in Example 18 to produce the-above compound from-the compound (14) synthesized in Example 8.

Example 31

Synthesis of (E)-4-[4-(4-fluorophenyl)methylphenyl]-1-1-(3-phenyl-2-propenyl)-4-piperidinol (37)

The same procedure was followed as in Example 11 to produce the above compound from the compound (15) synthesized in Example 9.

Example 32

Synthesis of 4-[4-(4-fluorophenyl)methylphenyl]-1-(2-phenyl-2-oxoethyl)-4-piperidinol (38)

The same procedure was followed as in Example 11 to produce the above compound from the compound (15) synthesized in Example 9 and phenacyl bromide.

Example 33

Synthesis of 4-[4-(4-fluorophenyl)methylphenyl]-1-(2-hydroxy-3-phenoxy)propyl-4-piperidinol (39)

The same procedure was followed as in Example 18 to produce the above compound from the compound (15) synthesized in Example 9.

Example 34

Synthesis of 1-(2-phenyl-2-oxoethyl)-4-(4-phenyl)phenyl-4-piperidinol (40)

The same procedure was followed as in Example 11 to produce the above compound from the compound (13) synthesized in Example 7 and phenacyl bromide.

Example 35

Synthesis of 1-(2-hydroxy-3-phenoxy)propyl-4-(4-phenyl)phenyl-4-piperidinol (41)

The same procedure was followed as in Example 18 to produce the above compound from the compound (13) synthesized in Example 7.

Example 36

Synthesis of (S)-4-(3-fluoro-4-phenyl)phenyl-1-(2-hydroxy-3-phenoxy)propyl-4-piperidinol (42)

The same procedure was followed as in Example 18 to produce the above compound from the compound (12) synthesized in Example 6 and (S)-(+)-1,2-epoxy-3-phenoxypropane.

Example 37

Synthesis of (R)-4-(3-fluoro-4-phenyl)phenyl-1-(2-hydroxy-3-phenoxy)propyl-4-piperidinol (43)

The same procedure was followed as in Example 18 to produce the above compound from the compound (12) synthesized in Example 6 and (R)-(−)-1,2-epoxy-3-phenoxypropane.

Example 38

Synthesis of 1-(2-hydroxy-2-phenyl)ethyl-4-(4-phenyl)phenyl-4-piperidinol (44)

To a 5 ml of methanol solution of 124 mg of the compound (40) synthesized in Example 34, 18 mg of sodium borohydride was added under ice cooling and stirred for 1 hour. To the reaction mixture, 8 ml of ice water was added and extraction performed with ethyl acetate. The extract was dried, filtered, then concentrated under reduced pressure to obtain a residue which was then purified by silica gel column chromatography (chloroform:methanol=20:1) to obtain 111 mg of the above-referenced compound (44) (yield 90%).

Example 39

Synthesis of (S)-4-(4-phenoxy)phenyl-1-(2-hydroxy-3-phenoxy)propyl-4-piperidinol (45)

The same procedure was followed as in Example 18 to produce the above compound from the compound (14) synthesized in Example 8 and (S)-(+)-1,2-epoxy-3-phenoxypropane.

Example 40

Synthesis of (R)-4-(4-phenoxy)phenyl-1-(2-hydroxy-3-phenoxy)propyl-4-piperidinol (46)

The same procedure was followed as in Example 18 to produce the above compound from the compound (14) synthesized in Example 8 and (R)-(−)-1,2-epoxy-3-phenoxypropane.

Example 41

Synthesis of (S)-4-[4-(4-fluorophenyl)methylphenyl]-1-(2-hydroxy-3-phenoxy)propyl-4-piperidinol (47)

The same procedure was followed as in Example 18 to produce the above compound from the compound (15) synthesized in Example 9 and (S)-(+)-1,2-epoxy-3-phenoxypropane.

Example 42

Synthesis of (R)-4-[4-(4-fluorophenyl) methylphenyl]-1-(2-hydroxy-3-phenoxy)propyl-4-piperidinol (48)

The same procedure was followed as in Example 18 to produce the above compound from the compound (15) synthesized in Example 9 and (R)-(−)-1,2-epoxy-3-phenoxypropane.

Example 43

Synthesis of 4-(4-phenoxy)phenyl-1-(1-phenyl-1-cyclopropane)methyl-4-piperidinol (49)

The same procedure was followed as in Example 11 to produce the above compound from the compound (14) synthesized in Example 8 and 1-phenyl-1-cyclopropanemethyl bromide.

Example 44

Synthesis of 4-(4-phenoxy)phenyl-1-(trans-2-phenyl-1-cyclopropylmethyl)-4-piperidinol (50)

The same procedure was followed as in Example 11 to produce the above compound from the compound (14) synthesized in Example 8 and trans-2-phenyl-1-cyclopropylmethyl bromide.

Example 45

Synthesis of 4-[4-(4-fluorophenyl)methylphenyl]-1-(1-phenyl-1-cyclopropane)methyl-4-piperidinol (51)

The same procedure was followed as in Example 11 to produce the above compound from the compound (15) synthesized in Example 9 and 1-phenyl-1-cyclopropanemethyl bromide.

Example 46

Synthesis of 4-[4-(4-fluorophenyl)methylphenyl]-1-(trans-2-phenyl-1-cyclopropylmethyl)-4-piperidinol (52)

The same procedure was followed as in Example 11 to produce the above compound from the compound (15) synthesized in Example 9 and trans-2-phenyl-1-cyclopropylmethyl bromide.

Example 47

Synthesis of N-(trans-2-phenyl-1-cyclopropyl)-4-hydroxy-4-(4-phenoxy)phenyl-1-piperidinacetamide (53)

The same procedure was followed as in Example 11 to produce the above compound from the compound (14) synthesized in Example 8 and 2-bromo-N-(trans-2-phenylcyclopropyl)acetamide [N. Bodor et al., J. Pharm. Sci., 80, 255 (1991)].

Example 48

Synthesis of N-(trans-2-phenyl-1-cyclopropyl)-4-[4-(4-fluorophenyl)methylphenyl]-4-hydroxy-1-piperidinacetamide (54)

The same procedure was followed as in Example 11 to produce the above compound from the compound (15) synthesized in Example 9 and 2-bromo-N-(trans-2-phenylcyclopropyl)acetamide.

Example 49

Synthesis of N-(2,6-dimethylphenyl)-4-hydroxy-4-(4-phenoxy)phenyl-1-piperidinacetamide (55)

The same procedure was followed as in Example 11 to produce the above compound from the compound (14) synthesized in Example 8 and N-(2,6-dimethylphenyl)-2-bromoacetamide [I. Mezo et al., J. Label. Compounds, 8, 859 (1972)].

Example 50

Synthesis of N-(2,6-dimethylphenyl)-4-[4-(4-fluorophenyl)methylphenyl]-4-hydroxy-1-piperidinacetamide (56)

The same procedure was followed as in Example 11 to produce the above compound from the compound (15) synthesized in Example 9 and N-(2,6-dimethylphenyl)-2-bromoacetamide.

Example 51

Synthesis of N-(1-phenyl)cyclopropyl-4-hydroxy-4-(4-phenoxy)phenyl-1-piperidinacetamide (57)

The same procedure was followed as in Example 11 to produce the above compound from the compound (14) synthesized in Example 8 and N-(1-phenyl)cyclopropyl-2-bromoacetamide.

Example 52

Synthesis of N-(1-phenyl)cyclopropyl-4-hydroxy-4-[4-(4-fluorophenyl)methylphenyl]-1-piperidinacetamide (58)

The same procedure was followed as in Example 11 to produce the above compound from the compound (15) synthesized in Example 9 and N-(1-phenyl)cyclopropyl-2-bromoacetamide synthesized according to the method reported by Kirino et al. [Japanese Unexamined Patent Publication No. 56-26854 (1981)].

Example 53

Synthesis of (E)-4-[4-(4-fluoro)phenoxy]phenyl-1-(3-phenyl-2-propenyl)-4-piperidinol (59)

The same procedure was followed as in Example 11 to produce the above compound from the compound (16) synthesized in Example 10.

Example 54

Synthesis of 4-[4-(4-fluoro)phenoxy]phenyl-1-(2-phenyl-2-oxoethyl)-4-piperidinol (60)

The same procedure was followed as in Example 11 to produce the above compound from the compound (16) synthesized in Example 10 and phenacyl bromide.

Example 55

Synthesis of (S)-4-[4-(4-fluoro)phenoxy]phenyl-1-(2-hydroxy-3-phenoxy)propyl-4-piperidinol (61)

The same procedure was followed as in Example 18 to produce the above compound from the compound (16) synthesized in Example 10 and (S)-(+)-1,2-epoxy-3-phenoxypropane.

The physical data of the compounds obtained in the Reference Examples and Examples are shown in Table I.

TABLE I

| Compound No. | Chemical Structure | Property | IR (CHCl₃) | ¹H-NMR(CDCl₃) |
|---|---|---|---|---|
| 1 | 4-(2-fluoro-biphenyl-4-yl)-1-benzyl-piperidin-4-ol | Oily substance | 2946, 2817, 1706, 1483, 1406, 1367, 1345, 1119 | 1.76(2H, m), 2.18(2H, m), 2.48(2H, m), 2.79–2.83(2H, m), 3.60(2H, s), 7.29–7.45(11H, m), 7.54(2H, d) |
| 2 | 4-(biphenyl-4-yl)-1-benzyl-piperidin-4-ol | Pale yellow crystal | 2946, 2818, 1706, 1601, 1486, 1454, 1367, 1344, 1115 | 1.76–1.80(2H, m), 2.21(2H, m), 2.51(2H, m), 2.81(2H, m), 3.60(2H, s), 7.28–7.44(8H, m), 7.58(6H, m) |
| 3 | 4-(4-phenoxyphenyl)-1-benzyl-piperidin-4-ol | Oily substance | 2946, 2818, 2399, 1704, 1590, 1506, 1490, 1106 | 1.76(2H, m), 2.15(2H, m), 2.58(2H, m), 2.77–2.81(2H, m), 3.58(2H, s), 6.96–7.02(4H, m), 7.09(1H, t), 7.27–7.37(7H, m), 7.47(2H, d) |
| 4 | 4-[4-(4-fluorobenzyl)phenyl]-1-benzyl-piperidin-4-ol | Oily substance | 2950, 2816, 1711, 1603, 1508, 1367, 1344, 1157, 1110, 1043 | 1.73(2H, m), 2.14(2H, m), 2.45(2H, m), 2.75(2H, m), 3.58(2H, s), 3.93(2H, s), 6.96(2H, t), 7.11–7.15(4H, m), 7.27–7.37(5H, m), 7.43(2H, d) |
| 5 | 4-[4-(4-fluorophenoxy)phenyl]-1-benzyl-piperidin-4-ol | Pale yellow oily substance | 3020, 2817, 1706, 1603, 1498, 929 | 1.73–1.77(2H, m), 2.11–2.18(2H, m), 2.50–2.65(2H, m), 2.78–2.80(2H, m), 3.58(2H, s), 6.92–7.07(4H, m), 7.26–7.37(7H, m), 7.46(2H, dd) |
| 6 | 4-(2-fluoro-biphenyl-4-yl)-1-Boc-piperidin-4-ol | Colorless crystal | 2401, 1676, 1482, 1426, 1368, 1164, 1032, 931 | 1.49(9H, s), 1.58(1H, s), 1.73–1.77(2H, m), 1.99–2.04(2H, m), 3.22–3.28(2H, m), 4.05–4.13(2H, m), 7.26–7.30(2H, m), 7.36–7.38(1H, m), 7.42–7.46(3H, m), 7.53–7.56(2H, m) |

TABLE I-continued

| # | Structure | Appearance | IR | NMR |
|---|---|---|---|---|
| 7 | 4-(4-biphenyl)-4-hydroxy-1-Boc-piperidine | Colorless crystal | 1676, 1486, 1431, 1367, 1168, 1139, 1031 | 1.49(9H, s), 1.57(1H, s), 1.76–1.80(2H, m), 2.02–2.07(2H, m), 3.24–3.31(2H, m), 4.03–4.13(2H, m), 7.34(1H, t), 7.43(2H, dt), 7.53–7.61(6H, m) |
| 8 | 4-(2-fluoro-4-biphenyl)-4-hydroxy-piperidine | Colorless crystal | 2926, 1621, 1554, 1484, 1415, 1359, 1282, 1175, 1133, 964 | 2.46–2.48(2H, m), 3.12(2H, t), 3.55–3.56(2H, m), 6.23(1H, t), 7.17(1H, d), 7.23–7.26(1H, m), 7.33–7.46(4H, m), 7.56(2H, d) |
| 9 | 4-(3-fluoro-4-biphenyl)-4-hydroxy-piperidine | Colorless crystal | 2939, 1624, 1483, 1446, 1418, 1317, 1271, 1134, 953 | 1.65(2H, dt), 1.86–1.89(2H, m), 2.66(1H, t), 2.76(2H, dd), 3.19–3.22(2H, m), 7.01(1H, dd), 7.07(1H, dd), 7.34–7.44(4H, m), 7.52–7.55(2H, m) |
| 10 | 4-(4-biphenyl)-1,2,3,6-tetrahydropyridine | Pale yellow crystal | 2926, 2360, 1600, 1487, 1438, 1359, 1317, 1144, 1007 | 2.48–2.51(2H, m), 3.13(2H, t), 3.56(2H, dt), 6.19–6.21(1H, m), 7.33(1H, dt), 7.41–7.47(4H, m), 7.55–7.61(4H, m) |
| 11 | 4-(4-biphenyl)-piperidine | Colorless crystal | 2938, 1600, 1522, 1486, 1446, 1318, 1136, 1008 | 1.68(2H, dt), 1.86–1.89(2H, m), 2.67(1H, d), 2.77(2H, dd), 3.20–3.23(2H, m), 7.26–7.34(3H, m), 7.42(2H, t), 7.53–7.59(4H, m) |
| 12 | 4-(2-fluoro-4-biphenyl)-4-hydroxy-piperidine | Colorless crystal | 3589, 2950, 1484, 1406, 1320, 1270, 1134, 1010 | 1.75–1.78(2H, m), 2.01–2.08(2H, m), 2.99–3.02(2H, m), 3.10–3.16(2H, m), 7.31–7.38(3H, m), 7.42–7.46(3H, m), 7.54–7.56(2H, m) |
| 13 | 4-(4-biphenyl)-4-hydroxy-piperidine | Pale yellow crystal | 2948, 2840, 1702, 1600, 1486, 1438, 1364, 1320, 1132, 1017 | 1.78(2H, m), 2.07(2H, m), 2.97–3.01(2H, m), 3.15(2H, m), 7.31–7.35(1H, m), 7.59–7.60(6H, m) |
| 14 | 4-hydroxy-4-(4-phenoxyphenyl)-piperidine | Oily substance | 2949, 1702, 1589, 1507, 1490, 1320, 1170, 1132, 1014 | 1.76(2H, m), 2.02(2H, m), 2.96–2.99(2H, m), 3.12(2H, m), 7.00(4H, dd), 7.10(1H, t), 7.33(2H, t), 7.46(2H, d) |

TABLE I-continued

| Compound No. | Chemical Structure | Property Melting point (Recrystallization solvent) | IR(KBr) | $^1$H-NMR(CDCl$_3$) | Elementary analysis |
|---|---|---|---|---|---|
| 15 | 4-fluorobenzyl-phenyl-piperidinol structure | Colorless crystal | 2949, 2842 1709, 1603 1508, 1438 1320, 1157 1131, 1018 | 1.72(2H, m), 2.00(2H, m), 2.93–2.96(2H, m), 3.11(2H, s), 3.94(2H, s), 6.96(2H, dd), 7.12–7.16(4H, m), 7.42(2H, d) | |
| 16 | 4-fluorophenoxy-phenyl-piperidinol structure | Pale yellow crystal | 3020, 2949 1706, 1603 1499, 1194 1169, 1131 1090, 1013 | 1.73–1.77(2H, m), 1.98–2.05(2H, m), 2.96–2.99(2H, m), 3.08–3.15(2H, m), 6.93–7.05(6H, m), 7.46(2H, d) | |
| 17 | biphenyl-F-piperidinol-cinnamyl structure | Colorless crystal (fumarate) 107–109° C. (methanol/ether) | (fumarate) 3384, 3030 2934, 2576 1701, 1582 1485, 1449 1407, 1272 | 1.60(1H, s), 1.79–1.82(2H, m), 2.20(2H, dt), 2.51(2H, d), 2.91–2.94(2H, m), 3.25(2H, d), 6.33(1H, dt), 6.57(1H, d), 7.23–7.45(11H, m), 7.54(2H, d) | C$_{30}$H$_{30}$NO$_5$F·¼H$_2$O (fumarate)  C    H    N  Calcd: 70.92 5.95 2.76  Found: 70.99 5.97 2.83 |
| 18 | biphenyl-F-piperidine-cinnamyl structure | Colorless crystal (hydrochloride) 236–237° C. (methanol/ether) | (hydrochloride) 3484, 2926 2633, 1624 1581, 1484 1419, 1271 1135, 1066 | 1.79–1.92(4H, m), 2.12(2H, dt), 2.56(1H, dt), 3.13–3.15(2H, m), 3.21(2H, d), 6.33(1H, dt), 6.57(1H, d), 7.03(1H, d), 7.08(1H, d), 7.23–7.26(2H, m), 7.29–7.44(7H, m), 7.53(2H, dd) | C$_{26}$H$_{27}$NClF·1 H$_2$O (hydrochloride)  C    H    N  Calcd: 73.31 6.39 3.29  Found: 73.36 6.70 3.28 |

TABLE I-continued

| | | | | |
|---|---|---|---|---|
| 19 | 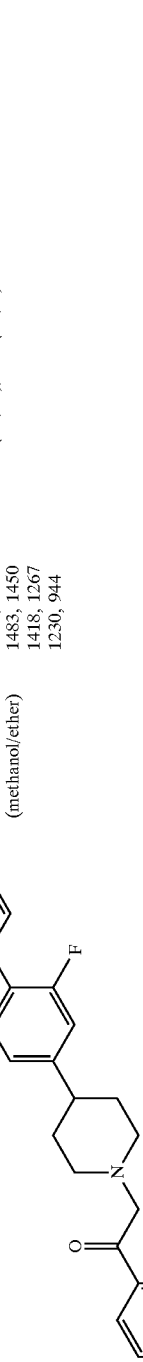 | Colorless crystal (hydrochloride) 211–212° C. (methanol/ether) | (hydrochloride) 3430, 2921 2628, 1702 1625, 1599 1483, 1450 1418, 1267 1230, 944 | 1.88–1.97(4H, m), 2.32(2H, dt), 2.53–2.86(1H, m), 3.13–3.16(2H, m), 3.85(2H, s), 7.03(1H, d), 7.08(1H, d), 7.34–7.58(9H, m), 8.04(2H, d) | $C_{25}H_{25}NOClF$ (hydrochloride)<br>C H N<br>Calcd: 73.25 6.15 3.42<br>Found: 73.03 6.14 3.38 |
| 20 | 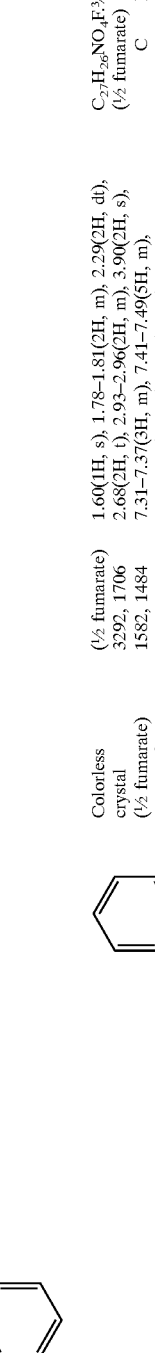 | Colorless crystal (½ fumarate) 172–174° C. (methanol/ether) | (½ fumarate) 3292, 1706 1582, 1484 1450, 1407 1266, 1226 975, 944 | 1.60(1H, s), 1.78–1.81(2H, m), 2.29(2H, d), 2.68(2H, t), 2.93–2.96(2H, m), 3.90(2H, s), 7.31–7.37(3H, m), 7.41–7.49(5H, m), 7.54–7.60(3H, m), 8.03(2H, d) | $C_{27}H_{26}NO_4F \cdot \text{¾}H_2O$ (½ fumarate)<br>C H N<br>Calcd: 70.35 5.68 3.04<br>Found: 70.85 5.88 3.06 |
| 21 | 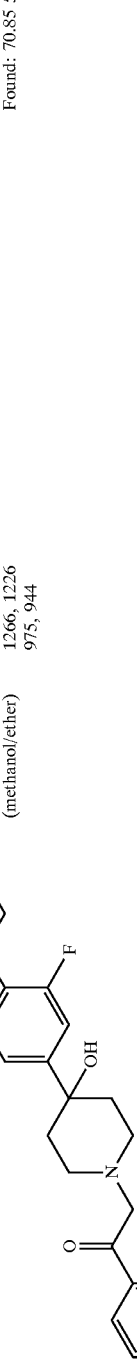 | Colorless crystal (fumarate) 203–205° C. (methanol/ether) | (fumarate) 3390, 2938 1683, 1602 1570, 1516 1484, 1367 1263, 1174 | 1.60(1H, s), 1.77–1.80(2H, m), 2.28(2H, d), 2.66(2H, t), 2.92–2.95(2H, m), 3.84(2H, s), 3.88(3H, s), 6.95(2H, d), 7.31–7.37(3H, m), 7.41–7.45(3H, m), 7.53–7.55(2H, m), 8.04(2H, d) | $C_{30}H_{30}NO_7F$ (fumarate)<br>C H N<br>Calcd: 67.28 5.65 2.62<br>Found: 67.36 5.60 2.60 |

TABLE I-continued

| | | | | | |
|---|---|---|---|---|---|
| 22 | 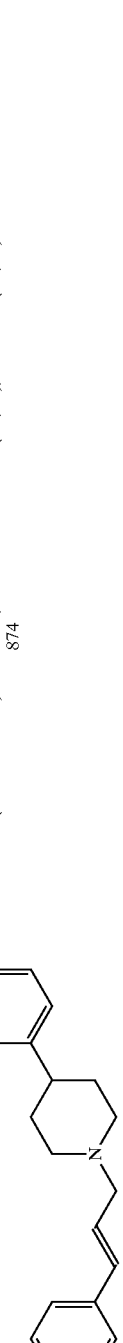 | Colorless crystal (hydrochloride) 235–238° C. (methanol/ether) | (hydrochloride) 3425, 3028 2933, 2508 1600, 1487 1450, 982 874 | 1.88(4H, m), 2.13(2H, dt), 2.55–2.57(1H, m), 3.13–3.16(2H, m), 3.22(2H, d), 6.31–6.38(1H, m), 6.55(1H, d), 7.23–7.26(2H, m), 7.30–7.33(4H, m), 7.39–7.43(4H, m), 7.52–7.58(4H, m) | $C_{26}H_{28}NCl$ (hydrochloride)<br>C H N<br>Calcd: 80.08 7.24 3.59<br>Found: 80.00 7.22 3.56 |
| 23 | 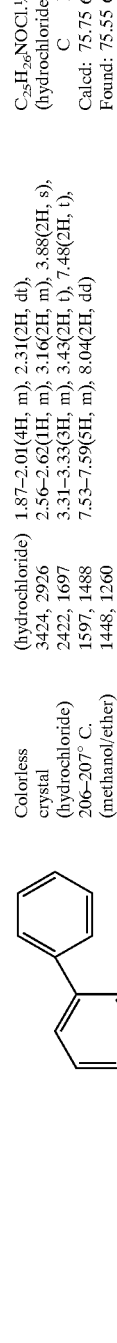 | Colorless crystal (hydrochloride) 206–207° C. (methanol/ether) | (hydrochloride) 3424, 2926 2422, 1697 1597, 1488 1448, 1260 1230, 962 | 1.87–2.01(4H, m), 2.31(2H, dt), 2.56–2.62(1H, m), 3.16(2H, m), 3.88(2H, s), 3.31–3.33(3H, m), 3.43(2H, t), 7.48(2H, t), 7.53–7.59(5H, m), 8.04(2H, dd) | $C_{25}H_{26}NOCl \cdot 1/4 H_2O$ (hydrochloride)<br>C H N<br>Calcd: 75.75 6.61 3.53<br>Found: 75.55 6.67 3.46 |
| 24 |  | Colorless crystal (1/2 fumarate) 193–194° C. (methanol/ether) | (1/2 fumarate) 3188, 2935 1577, 1497 1372, 1242 1048, 989 | 1.80–1.83(2H, m), 2.11–2.25(2H, m), 2.56(1H, dt), 2.64(2H, d), 2.81–2.86(2H, m), 2.94–2.97(1H, m), 4.02(2H, d), 4.15(1H, m), 6.93–6.99(3H, m), 7.26–7.38(5H, m), 7.42–7.46(3H, m), 7.55(2H, d) | $C_{28}H_{30}NO_5F_1 \cdot 1/2$ fumarate<br>C H N<br>Calcd: 69.48 6.25 2.89<br>Found: 69.95 6.35 2.89 |
| 25 |  | Pale brown crystal (fumarate) 192–195° C. (methanol/ether) | (fumarate) 3402, 3030 2945, 2520 1712, 1582 1484, 1420 1271, 1171 | 0.84–0.89(1H, m), 0.97–1.02(1H, m), 1.28–1.30(1H, dt), 1.71(1H, dt), 1.82–1.87(4H, m), 2.14–2.16(2H, m), 2.43–2.47(1H, m), 2.51–2.60(2H, m), 3.20(2H, m), 7.02(1H, d), 7.07(2H, d), 7.16(1H, t), 7.25–7.45(7H, m), 7.53(2H, d) | $C_{31}H_{32}NO_4F \cdot 1/4 H_2O$ (fumarate)<br>C H N<br>Calcd: 73.57 6.37 2.77<br>Found: 73.62 6.37 2.76 |

TABLE I-continued

| No. | Structure | Appearance | IR | NMR | Formula |
|---|---|---|---|---|---|
| 26 | (4-phenylphenyl-2-fluoro-4-hydroxypiperidine with N-CH2-cyclopropyl-phenyl) | Pale brown crystal (fumarate) 190–193° C. (methanol/ether) | (fumarate) 3370, 3028 2576, 1702 1582, 1484 1448, 1407 1271, 1174 | 0.77(2H, m), 0.90(2H, m), 1.67–1.70(2H, m), 2.06–2.08(2H, m), 2.39–2.44(2H, m), 2.65(2H, s), 2.89–2.91(2H, m), 7.18–7.22(1H, m), 7.26–7.45(10H, m), 7.53–7.54(2H, d). | $C_{31}H_{32}NO_5F \cdot \frac{1}{4}H_2O$ (fumarate)<br>C H N<br>Calcd: 71.32 6.18 2.68<br>Found: 71.38 6.17 2.68 |
| 27 | (4-biphenyl-piperidine with N-CH2-cyclopropyl-phenyl) | Pale brown crystal (hydrochloride) 201–203° C. (methanol/ether) | (hydrochloride) 3425, 3028 2941, 2670 1604, 1498 1487, 1450 1426, 958 | 0.84–0.89(1H, m), 0.97–1.01(1H, m), 1.25–1.32(1H, m), 1.69–1.73(1H, m), 1.82–1.89(4H, m), 2.15–2.17(2H, m), 2.43–2.60(3H, m), 3.20(2H, m), 7.07(2H, d), 7.15(1H, t), 7.24–7.34(3H, m), 7.40–7.44(3H, m), 7.52–7.58(5H, m) | $C_{27}H_{30}NCl \cdot \frac{1}{2}H_2O$ (hydrochloride)<br>C H N<br>Calcd: 79.39 7.40 3.43<br>Found: 79.13 7.73 3.40 |
| 28 | (4-biphenyl-piperidine with N-CH2-cyclopropyl-phenyl, isomer) | Brown crystal (hydrochloride) 230–232° C. (methanol/ether) | (hydrochloride) 3424, 3024 2928, 2512 1601, 1486 1449, 1158 968, 838 | 0.75–0.76(2H, m), 0.87–0.89(2H, m), 1.69–1.75(4H, m), 2.05(2H, m), 2.43–2.47(1H, m), 2.61(2H, s), 3.08–3.11(2H, m), 7.18(1H, t), 7.25–7.33(3H, m), 7.37–7.43(5H, m), 7.49–7.57(5H, m) | $C_{27}H_{30}NCl$ (hydrochloride)<br>C H N<br>Calcd: 80.27 7.48 3.47<br>Found: 79.97 7.45 3.45 |
| 29 | (4-biphenyl-piperidine with N-CH2-CH(OH)-CH2-O-phenyl) | Colorless crystal (hydrochloride) 209–211° C. (methanol/ether) | (hydrochloride) 3281, 2930 2527, 1598 1497, 1488 1250, 1078 1046 | 1.79–1.91(5H, m), 2.18(1H, dt), 2.46(1H, dt), 2.55–2.65(2H, m), 3.01–3.04(1H, m), 3.16–3.19(1H, m), 3.98–4.05(2H, m), 4.15(1H, dt), 6.93–6.98(3H, m), 7.26–7.34(5H, m), 7.42(2H, t), 7.53–7.59(4H, m) | $C_{26}H_{30}NO_2Cl$ (hydrochloride)<br>C H N<br>Calcd: 73.66 7.13 3.30<br>Found: 73.50 7.09 3.27 |

TABLE I-continued

| | Structure | Appearance / mp / solvent | IR | NMR | Formula / Analysis |
|---|---|---|---|---|---|
| 30 | 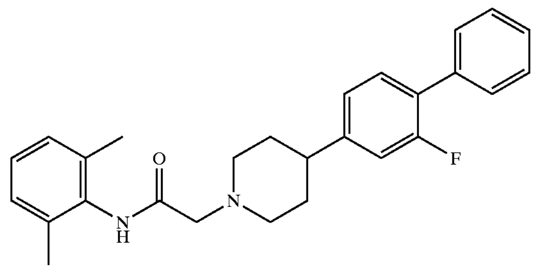 | Colorless crystal (hydrochloride) 219–221° C. (acetonitrile) | (hydrochloride) 3414, 3200 3032, 2498 1699, 1534 1484, 1421 1267, 1237 | 1.81–1.88(2H, m), 1.97–2.00(2H, m), 2.26(6H, s), 2.47(2H, d), 2.60–2.66(1H, m), 3.16–3.19(2H, m), 3.25(2H, s), 6.99–7.09(5H, m), 7.35–7.45(4H, m), 7.52–7.54(2H, m), 8.73(1H, m) | $C_{27}H_{30}N_2O$ ClF (hydrochloride)<br>   C   H   N<br>Calcd: 71.59 6.68 6.18<br>Found: 71.31 6.65 6.15 |
| 31 | 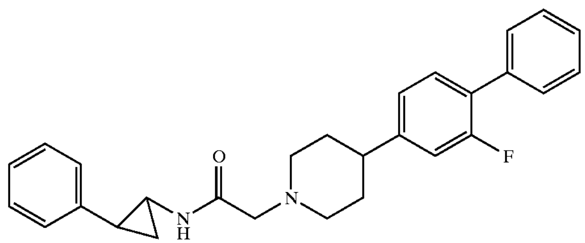 | Colorless crystal (hydrochloride) 179–181° C. (methanol/ether) | (hydrochloride) 3430, 3219 3032, 1684 1560, 1485 1420, 1272 1132, 1076 | 1.19–1.32(2H, m), 1.73–1.82(2H, m), 1.91–1.94(2H, m), 2.06–2.11(1H, m), 2.32(2H, t), 2.57(1H, tt), 2.95–2.97(3H, m), 3.04(2H, s), 6.99–7.09(2H, m), 7.16–7.20(2H, m), 7.26–7.31(3H, m), 7.35–7.45(4H, m), 7.54(2H, s) | $C_{32}H_{33}N_2O_5F$ (hydrochloride)<br>   C   H   N<br>Calcd: 70.57 6.11 5.14<br>Found: 70.31 6.17 5.19 |
| 32 | 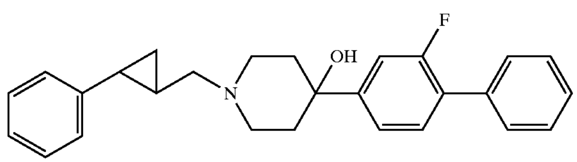 | Pale brown crystal (fumarate) 201–203° C. (methanol/ether) | (fumarate) 1700, 1586 1484, 1407 1357, 1254 1182, 983 | 0.87(1H, m), 1.00(1H, m), 1.26–1.34(1H, m), 1.73(1H, m), 1.77(2H, m), 2.20(2H, m), 2.46–2.62(4H, m), 2.95–3.17(2H, m), 7.08(2H, d), 7.14(1H, t), 7.24–7.27(2H, m), 7.31–7.45(6H, m), 7.53–7.55(2H, d) | $C_{31}H_{32}NO_5F$ (fumarate)<br>   C   H   N<br>Calcd: 71.94 6.23 2.71<br>Found: 71.77 6.13 2.67 |
| 33 | 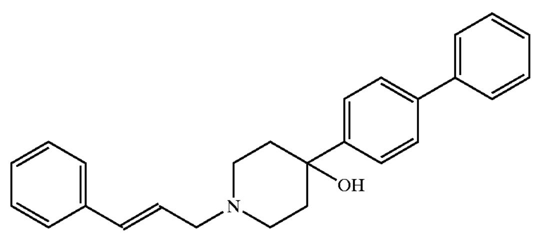 | Colorless crystal (fumarate) 200–202° C. (2-Propanol/diisopropyl ether) | (fumarate) 3411, 1700 1641, 1570 1487, 1389 1244, 1202 | 1.81–1.84(2H, m), 2.21–2.29(2H, m), 2.52–2.57(2H, m), 2.90–2.95(2H, m), 3.27(2H, d), 6.34(1H, d), 6.57(1H, d), 7.21–7.45(8H, m), 7.54–7.59(6H, m) | $C_{31}H_{32}NO_5F \cdot \frac{1}{4}H_2O$ (fumarate)<br>   C   H   N<br>Calcd: 73.53 6.38 2.86<br>Found: 73.54 6.39 2.86 |

TABLE I-continued

| | Structure | Properties | IR | NMR |
|---|---|---|---|---|
| 34 | 4-(4-phenoxyphenyl)-4-hydroxy-1-cinnamyl-piperidine | Colorless crystal (fumarate) 93–97° C. (2-Propanol/ether) | (fumarate) 1702, 1589 1508, 1490 1372, 1287 1240, 1171 984 | 1.80(2H, m), 2.19(2H, m), 2.51(2H, m), 2.90(2H, m), 3.25(2H, d), 6.33(1H, dt), 6.56(1H, d), 6.97–7.02(4H, m), 7.10(1H, t), 7.21–7.35(5H, m), 7.39(2H, d), 7.47(2H, d) | — |
| 35 | 4-(4-phenoxyphenyl)-4-hydroxy-1-phenacyl-piperidine | Colorless crystal (½ fumarate) 173–175° C. (methanol/ether) | (½ fumarate) 1697, 1589 1508, 1490 1450, 1368 1292, 1240 1234, 1171 | 1.79(2H, m), 2.27(2H, m), 2.67(2H, m), 2.92(2H, m), 3.89(2H, s), 6.96–7.02(4H, m), 7.10(1H, t), 7.33(2H, t), 7.45(4H, m), 7.57(1H, t), 8.02(2H, d) | — |
| 36 | 4-(4-phenoxyphenyl)-4-hydroxy-1-(2-hydroxy-3-phenoxypropyl)-piperidine | Colorless crystal (½ fumarate) 180–182° C. (methanol/ether) | (½ fumarate) 1588, 1508 1490, 1368 1290, 1240 1172, 1044 984 | 1.81(2H, m), 2.15(2H, m), 2.55(1H, m), 2.63(2H, d), 2.79–2.83(2H, m), 2.93(1H, m), 4.01(2H, d), 4.14(1H, dt), 6.93–7.02(7H, m), 7.10(1H, t), 7.26–7.35(4H, m), 7.46(2H, d) | — |
| 37 | 4-[4-(4-fluorobenzyl)phenyl]-4-hydroxy-1-cinnamyl-piperidine | Colorless foam (fumarate) | (fumarate) 1700, 1600 1578, 1508 1364, 1221 1158, 984 | 1.76(2H, m), 2.18(2H, m), 2.51(2H, m), 2.89(2H, m), 3.24(2H, d), 3.93(2H, s), 6.32(1H, d), 6.55(1H, d), 6.96(2H, d), 7.12–7.44(11H, m) | — |
| 38 | 4-[4-(4-fluorobenzyl)phenyl]-4-hydroxy-1-phenacyl-piperidine | Colorless crystal (½ fumarate) 75–78° C. (methanol/ether) | (½ fumarate) 1699, 1599 1582, 1508 1450, 1372 1261, 1224 1158 | 1.76(2H, m), 2.26(2H, m), 2.65(2H, m), 2.91(2H, m), 3.89(2H, s), 3.94(2H, s), 6.96(2H, t), 7.12–7.16(4H, m), 7.42–7.48(4H, m), 7.57(1H, t), 8.02(2H, d) | — |

TABLE I-continued

| # | Structure | Properties | IR | NMR | Analysis |
|---|---|---|---|---|---|
| 39 | (4-fluorobenzyl-phenyl piperidinol with hydroxypropyl phenoxy) | Colorless crystal (½ fumarate) 160–161° C. (methanol/ether) | (½ fumarate) 1600, 1574 1508, 1368 1245, 1043 984 | 1.78(2H, m), 2.14(2H, m), 2.55(1H, m), 2.62(2H, d), 2.78–2.85(2H, m), 2.92(2H, m), 3.94(2H, s), 4.01(2H, d), 4.14(1H, tt), 6.92–6.99(5H, m), 7.12–7.17(4H, m), 7.26–7.30(2H, m), 7.42(2H, d) | — |
| 40 | (biphenyl piperidinol with phenacyl) | Yellow powder (½ fumarate) 178–180° C. (methanol/ether) | (½ fumarate) 1694, 1598 1582, 1487 1450, 1391 1260, 984 958 | 1.80–1.84(2H, m), 2.33(2H, m), 2.70(2H, m), 2.93–2.96(2H, m), 3.90(2H, s), 7.33–7.35(1H, m), 7.41–7.51(4H, m), 7.56–7.60(7H, m), 8.04(2H, d) | $C_{27}H_{27}NO_4 \cdot 5/4H_2O$ (½ fumarate)<br>  C    H    N<br>Calcd: 71.74 6.02 3.10<br>Found: 71.76 6.05 2.96 |
| 41 | (biphenyl piperidinol with hydroxypropyl phenoxy) | Colorless crystal (½ fumarate) 194–195° C. (methanol/ether) | (½ fumarate) 1599, 1572 1488, 1364 1291, 1244 1174, 1107 1079, 1046 984 | 1.82–1.86(2H, m), 2.14–2.28(2H, m), 2.58(1H, m), 2.65(2H, d), 2.78–2.89(2H, m), 2.94–2.97(1H, m), 4.02(2H, d), 4.13–4.19(1H, m), 6.93–6.98(3H, m), 7.27–7.36(3H, m), 7.44(2H, dd), 7.57–7.64(6H, m) | — |
| 42 | (2-fluorobiphenyl piperidinol with hydroxypropyl phenoxy) | Colorless crystal (½ fumarate) 191–192° C. (methanol/ether) [α]$_D$ −2.92° (C = 0.27, MeOH) | (½ fumarate) 1599, 1578 1497, 1485 1406, 1372 1290, 1174 1048, 989 | 1.57–1.83(2H, m), 2.11–2.25(2H, m), 2.56(1H, m), 2.64(2H, d), 2.80–2.81(2H, m), 2.83–2.84(1H, m), 4.02(2H, d), 4.12–4.18(1H, m), 6.93–6.98(3H, m), 7.27–7.39(5H, m), 7.44(3H, m), 7.54–7.56(2H, m) | $C_{28}H_{30}FNO_5$ (½ fumarate)<br>  C    H    N<br>Calcd: 70.13 6.31 2.92<br>Found: 70.19 6.18 2.99 |

TABLE I-continued

| | | | | | |
|---|---|---|---|---|---|
| 43 | 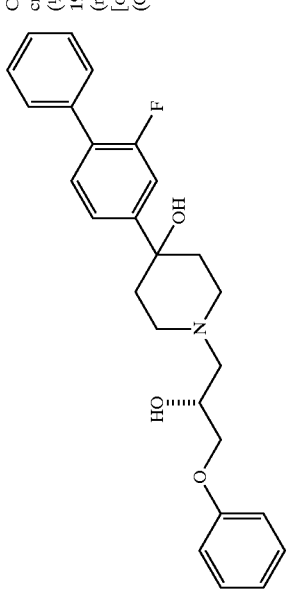 | Colorless crystal (½ fumarate) 190–192° C. (methanol/ether) [α]_D +2.92° (C = 0.28, MeOH) | (½ fumarate) 1576, 1497 1406, 1372 1289, 1241 1174, 1131 1048, 990 | 1.59–1.83(2H, m), 2.11–2.25(2H, m), 2.56(1H, m), 2.64(2H, m), 2.80–2.84(2H, m), 2.94–2.97(1H, m), 4.02(2H, d), 4.15(1H, m), 6.93–6.98(3H, m), 7.27–7.39(5H, m), 7.44(3H, dd), 7.55(2H, d) | $C_{28}H_{30}FNO_5$ (½ fumarate) Calcd: 70.13 6.31 2.92 Found: 70.10 6.19 2.97 C H N |
| 44 | 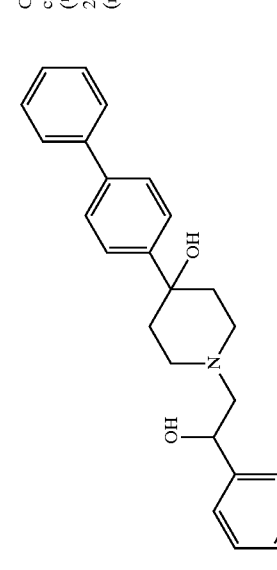 | Colorless crystal (½ fumarate) 215–216° C. (methanol/ether) | (½ fumarate) 1571, 1488 1450, 1363 1230, 1099 1065, 1044 984 | 1.86(2H, m), 2.17–2.30(2H, m), 2.52–2.67(3H, m), 2.74–2.77(1H, m), 2.87(1H, m), 3.08–3.11(1H, m), 4.79(1H, dd), 2.76–2.30(1H, m), 2.33(7H, m), 7.58–7.63(6H, m) | $C_{27}H_{29}NO_4 \cdot {}^{3}\!/\!4H_2O$ (½ fumarate) Calcd: 72.87 6.57 3.15 Found: 72.87 6.65 3.14 C H N |
| 45 | 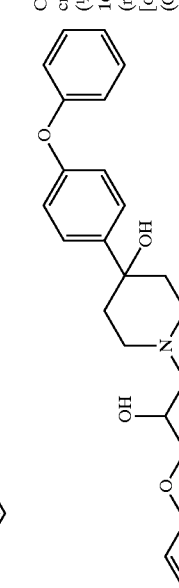 | Colorless crystal (½ fumarate) 161–162° C. (methanol/ether) [α]_D −7.03° (C = 1.30, MeOH) | (½ fumarate) 1588, 1490 1367, 1292 1240, 1172 1106, 1079 1043, 984 | 1.55–1.83(2H, m), 2.08–2.22(2H, m), 2.55(1H, m), 2.63(2H, d), 2.78–2.85(2H, m), 2.91–2.94(1H, m), 4.01(2H, d), 4.14(1H, m), 6.93–7.02(7H, m), 7.10(1H, t), 7.26–7.36(4H, m), 7.46(2H, ddd) | $C_{28}H_{31}NO_5 \cdot \!\!\tfrac{1}{2}H_2O$ (½ fumarate) Calcd: 69.12 6.42 2.88 Found: 69.04 6.48 2.88 C H N |
| 46 | 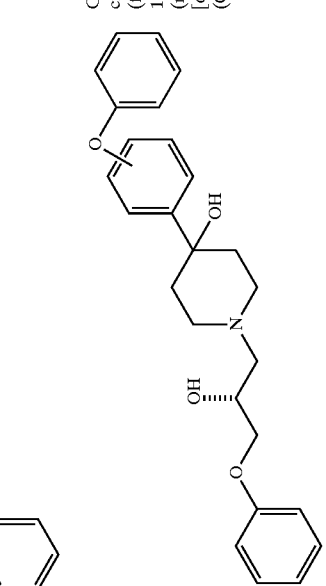 | Colorless crystal (fumarate) 160–162° C. (methanol/ether) [α]_D +7.03° (C = 1.13, MeOH) | (fumarate) 1588, 1508 1490, 1372 1292, 1243 1172, 1044 984 | 1.81(2H, m), 2.15(2H, m), 2.54(1H, dt), 3.45(2H, d), 2.78–2.86(2H, m), 2.93(1H, m), 4.01(2H, d), 4.14(1H, m), 6.93–7.03(7H, m), 7.11(1H, t), 7.26–7.36(4H, m), 7.47(2H, d) | $C_{28}H_{31}NO_6 \cdot {}^{3}\!/\!4H_2O$ (½ fumarate) Calcd: 68.49 6.36 2.85 Found: 68.74 6.41 2.90 C H N |

TABLE I-continued

| # | Structure | Properties | IR | NMR | Analysis |
|---|---|---|---|---|---|
| 47 | (structure: 4-[4-(4-fluorobenzyl)phenyl]-4-hydroxypiperidine with N-CH2-CH(OH)-CH2-O-phenyl) | Colorless crystal (½ fumarate) 178–180° C. (methanol/ether) [α]_D −7.96° (C = 1.07, MeOH) | (½ fumarate) 1600, 1570 1508, 1368 1247, 1222 1096, 1045 985 | 1.77–1.80(2H, m), 2.14(2H, m), 2.54(1H, m), 2.62(2H, d), 2.77–2.85(2H, m), 2.90–2.93(1H, m), 3.94(2H, s), 4.00(2H, dd), 4.11–4.16(1H, m), 6.92–6.99(5H, m), 7.12–7.17(4H, m), 7.26–7.30(2H, m), 7.42(2H, d) | $C_{29}H_{32}FNO_5$ (½ fumarate) C H N Calcd: 70.57 6.53 2.84 Found: 70.28 6.59 2.84 |
| 48 | (structure: same as 47, opposite stereochemistry) | Colorless crystal (½ fumarate) 178–179° C. (methanol/ether) [α]_D +7.96° (C = 1.24, MeOH) | (½ fumarate) 1600, 1569 1508, 1368 1247, 1222 1096, 1046 985 | 1.78(2H, m), 2.13(2H, m), 2.54(1H, m), 2.62(2H, d), 2.77–2.85(2H, m), 2.92(1H, m), 3.94(2H, s), 4.01(2H, d), 4.14(1H, m), 6.93–6.99(5H, m), 7.12–7.14(4H, m), 7.26–7.30(2H, m), 7.43(2H, d) | $C_{29}H_{32}FNO_5$ (½ fumarate) C H N Calcd: 70.57 6.53 2.84 Found: 70.33 6.58 2.84 |
| 49 | (structure: 4-(4-phenoxyphenyl)-4-hydroxypiperidine with N-CH2-cyclopropyl-phenyl) | Colorless crystal (½ fumarate) 152–154° C. (methanol/ether) | (½ fumarate) 3382, 1589 1508, 1490 1386, 1232 1172, 984 | 0.76(2H, m), 0.88(2H, m), 1.68(2H, m), 2.03(2H, d), 2.41(2H, d), 2.63(2H, s), 2.85(2H, m), 6.94–7.00(4H, m), 7.09(1H, t), 7.18(1H, t), 7.26–7.43(8H, m) | $C_{29}H_{31}NO_4 \cdot ¼H_2O$ (½ fumarate) C H N Calcd: 75.38 6.76 3.06 Found: 75.36 6.73 3.04 |
| 50 | (structure: same as 49 variant) | Colorless crystal (½ fumarate) 188–190° C. (methanol/ether) | (½ fumarate) 3383, 1588 1507, 1490 1388, 1232 1170, 982 | 0.84–0.89(1H, m), 0.97–1.02(1H, m), 1.26–1.28(1H, m), 1.71(1H, m), 1.78(2H, m), 2.17(2H, m), 2.49–2.61(4H, m), 2.95(2H, m), 6.96–7.16(8H, m), 7.23–7.26(2H, m), 7.33(2H, d), 7.46(2H, d) | $C_{29}H_{31}NO_4$ (½ fumarate) C H N Calcd: 76.13 6.83 3.05 Found: 76.32 6.90 3.05 |
| 51 | (structure: 4-[4-(4-fluorobenzyl)phenyl]-4-hydroxypiperidine with N-CH2-cyclopropyl-phenyl) | Colorless crystal (½ fumarate) 118–120° C. (methanol/ether) | (½ fumarate) 1579, 1508 1436, 1385 1368, 1297 1224, 1156 981 | 0.76(2H, m), 0.88(2H, m), 1.65(2H, m), 2.02(2H, m), 2.41(2H, d), 2.62(2H, s), 2.85(2H, m), 3.92(2H, s), 6.96(2H, t), 7.11–7.19(5H, m), 7.26–7.29(2H, m), 7.35–7.39(4H, m) | $C_{30}H_{32}FNO_3 \cdot 1H_2O$ (½ fumarate) C H N Calcd: 73.30 6.56 2.85 Found: 72.99 6.94 2.89 |

TABLE I-continued

| | Structure | Appearance | IR | NMR | Formula / Analysis |
|---|---|---|---|---|---|
| 52 | 4-[1-(4-fluorobenzyl)piperidin-4-yl]... (OH piperidine with 4-fluorobenzyl substituent on N, phenyl on benzyl) | Brown foam (fumarate) | 1695, 1508, 1416, 1298, 1220, 1158, 1109, 1094, 1041, 972 | 0.91(1H, m), 1.03(1H, m), 1.34(1H, m), 1.76–1.80(3H, m), 2.27(2H, m), 2.64(4H, m), 3.03(2H, m), 3.34–3.49(1H, brs), 3.93(2H, s), 6.96(2H, t), 7.70(2H, d), 7.11–7.16(5H, m), 7.23–7.27(2H, m), 7.42(2H, d) | — |
| 53 | (phenoxyphenyl piperidinol with cyclopropyl-phenyl amide) | Colorless crystal (½ fumarate) 112–114° C. (2-Propanol/ether) | 3417, 1680, 1589, 1508, 1490, 1367, 1289, 1239, 1171, 984 | 1.20(1H, m), 1.28(1H, m), 1.82(2H, m), 2.04–2.15(3H, m), 2.67–2.72(4H, m), 2.96(1H, m), 3.08(2H, s), 7.99–7.03(4H, m), 7.09–7.20(4H, m), 7.26–7.29(1H, m), 7.34(3H, m), 7.47(2H, d) | $C_{30}H_{32}N_2O_5 \cdot H_2O$ (½ fumarate) Calcd: C 69.48 H 6.22 N 5.40 Found: 69.52 6.26 5.39 |
| 54 | (4-fluorophenyl piperidinol with cyclopropyl-phenyl amide) | Colorless crystal (fumarate) 106–108° C. (2-Propanol/ether) | 3418, 1684, 1603, 1570, 1508, 1372, 1222, 984 | 1.19(1H, m), 1.28(1H, m), 1.79(2H, m), 2.04–2.14(3H, m), 2.66–2.72(4H, m), 2.95(2H, s), 3.67(2H, s), 3.95(2H, s), 6.97(2H, t), 7.12–7.20(7H, m), 7.26–7.36(2H, m), 7.43(2H, d) | $C_{33}H_{35}FN_2O_6$ (fumarate) Calcd: C 68.98 H 6.14 N 4.87 Found: 68.93 6.14 5.07 |
| 55 | (phenoxyphenyl piperidinol with 2,6-dimethylphenyl amide) | Colorless crystal (fumarate) 173–175° C. (methanol/ether) | 3426, 1690, 1643, 1589, 1548, 1508, 1490, 1239, 1172, 984 | 1.89(2H, m), 2.13–2.26(2H, m), 2.25(6H, s), 2.84–2.92(4H, m), 3.28(2H, s), 6.99–7.02(4H, m), 7.34(2H, t), 7.47(2H, d), 7.90–7.13(4H, m), 8.75(1H, brs) | $C_{31}H_{34}N_2O_7 \cdot ½H_2O$ (fumarate) Calcd: C 67.02 H 6.17 N 5.04 Found: 67.12 6.25 5.16 |
| 56 | (4-fluorobenzyl phenyl piperidinol with 2,6-dimethylphenyl amide) | Colorless crystal (fumarate) 174–176° C. (methanol/ether) | 3402, 3028, 2970, 1693, 1642, 1548, 1508, 1400, 1272, 1220 | 1.85(2H, m), 2.16(2H, m), 2.24(6H, s), 2.82–2.93(4H, m), 3.27(2H, s), 3.94(2H, s), 6.97(2H, t), 7.09–7.18(7H, m), 7.43(2H, d), 8.75(1H, brs) | $C_{33}H_{35}FN_2O_6$ (fumarate) Calcd: C 67.77 H 6.22 N 4.94 Found: 67.82 6.44 4.86 |

TABLE I-continued

| | Structure | Properties | IR | NMR | Analysis |
|---|---|---|---|---|---|
| 57 | [4-phenoxyphenyl-piperidin-4-ol with N-CH2-C(O)-NH-cyclopropyl(phenyl)] | Colorless crystal 121–124° C. (acetonitrile/ether) | (fumarate) 1683, 1589 1508, 1490 1457, 1396 1325, 1235 1172, 984 | 1.26–1.32(4H, m), 1.80–1.83(2H, m), 2.08–2.15(2H, m), 2.66–2.71(4H, m), 3.08(2H, s), 6.99–7.03(4H, m), 7.09–7.13(1H, t), 7.17–7.20(1H, m), 7.26–7.36(6H, m), 7.47(2H, d), 7.81(1H, brs) | $C_{32}H_{34}N_2O_7 \cdot \frac{1}{2}H_2O$ (fumarate) C H N Calcd: 67.71 6.04 4.93 Found: 67.85 6.06 4.98 |
| 58 | [4-(4-fluorobenzyl)phenyl-piperidin-4-ol with N-CH2-C(O)-NH-cyclopropyl(phenyl)] | Colorless crystal 156–157° C. (acetonitrile/ether) | (fumarate) 3044, 1680 1602, 1558 1508, 1401 1297, 1221 1157, 984 | 1.24–2.29(4H, m), 1.77–1.80(2H, m), 2.06–2.14(2H, m), 2.69(4H, m), 3.07(2H, s), 3.94(2H, s), 6.97(2H, dd), 7.12–7.21(5H, m), 7.24–7.30(4H, m), 7.42(2H, m), 7.80(1H, brs) | $C_{33}H_{35}FN_2O_6$ (fumarate) C H N Calcd: 68.98 6.14 4.87 Found: 68.86 6.50 4.59 |
| 59 | [4-(4-fluorophenoxy)phenyl-piperidin-4-ol with N-cinnamyl] | Colorless crystal (½ fumarate) mp. 148–150° C. (ether/methanol) | (½ fumarate) 1610, 1499 1248, 1215 1195, 1171 974 | 1.67–1.80(2H, m), 2.23–2.31(2H, m), 2.64–2.69(2H, m), 2.92–2.95(2H, m), 3.91(2H, s), 6.93–7.05(6H, m), 7.45–7.49(5H, m), 8.02(2H, d) | — |
| 60 | [4-(4-fluorophenoxy)phenyl-piperidin-4-ol with N-CH2-C(O)-phenyl] | Colorless crystal (fumarate) mp. 50–52° C. (ether/methanol) | (fumarate) 1695, 1598 1583, 1499 1495, 1450 1390, 1252 1215 | 1.81–1.84(2H, m), 2.32(2H, m), 2.64(2H, m), 2.81(2H, m), 3.35(2H, m), 6.34–6.40(1H, m), 6.58–6.62(1H, m), 6.93–7.08(6H, m), 7.28–7.45(5H, m), 7.97(2H, d) | — |
| 61 | [4-(4-fluorophenoxy)phenyl-piperidin-4-ol with N-CH2-CH(OH)-CH2-O-phenyl] | Colorless crystal (½ fumarate) mp. 48–50° C. (ether/methanol) $[\alpha]_D$ −5.45° (C = 1.1, MeOH) | (½ fumarate) 1599, 1588 1499, 1368 1293, 1247 1214, 1195 1173, 1044 | 1.51–1.82(2H, m), 2.07–2.21(2H, m), 2.54(1H, d), 2.63(2H, d), 2.79–2.85(2H, m), 2.91–2.94(1H, m), 4.01(1H, d), 4.11–4.17(1H, m), 6.93–7.08(9H, m), 7.26–7.31(2H, m), 7.42(2H, d) | — |

Inhibitory Effect of Veratrizine-induced Sodium Channel Activity

The membrane potential of the synaptozomes prepared from the brain membrane of Wistar rats (male, 10 to 12 weeks old) was measured by the method of Aiuchi et al. (t. Aiuchi et al: Biochimi. Biophys. Acta. 771, 228 (1984)) using a membrane potential sensitive fluorescent dye Rhodamine 6G to evaluate the effects of suppression of the compound on the veratrizine-inducing depolarization response. The results are shown in Table II.

TABLE II

| Compound No. | Anti-veratridine effect (inhibiting rate %) (compound 0.1 $\mu$M) |
|---|---|
| 17 | 26.8 |
| 18 | 13.1 |
| 19 | 12.9 |
| 20 | 20.2 |
| 21 | 18.6 |
| 23 | 11.3 |
| 24 | 23.8 |
| 25 | 57 |
| 26 | 30 |
| 27 | 41 |
| 28 | 24 |
| 29 | 40 |
| 31 | 14 |
| 32 | 27.3 |
| 33 | 12.8 |
| 34 | 29.9 |
| 35 | 27.7 |
| 36 | 28.6 |
| 37 | 39.7 |
| 38 | 18 |
| 39 | 18.7 |
| 40 | 23 |
| 41 | 23.7 |
| 42 | 21 |
| 43 | 21.2 |
| 45 | 19.8 |
| 46 | 19.8 |
| 47 | 39.5 |
| 48 | 22.7 |
| 49 | 18.9 |
| 50 | 33.4 |
| 53 | 32.3 |
| 54 | 20.4 |
| 55 | 28.3 |
| 57 | 40.1 |
| 58 | 11.3 |

T-Type Calcium Channel Inhibitory Effect

The hippocampal CA1 pyramidal cells were isolated from Wistar rats (female, 1 week old) according to the method reported by Takahashi et al. [K. Takahashi et al.; J. Pharmacol. Exp. Ther., 256, 169 (1991)] and the T-type calcium current under conditions of a fixed membrane potential was measured using the whole-cell configration of the patch clamp technique. The effects of the compounds were evaluated from the rate of suppression of the peak current after one minute of application using the concentration clamp method. The results are shown in Table III.

TABLE III

| Compound No. | T-type $Ca^{2+}$ channel inhibitory effect $IC_{50}$ ($\mu$M) |
|---|---|
| 17 | 1.9 |
| 20 | 3.0 |
| 34 | 1.7 |
| 39 | 1.3 |
| 42 | 0.55 |
| 43 | 1.4 |

Audiogenic Seizure Suppressing Effect

The audiogenic seizure suppressing effect of the compounds was evaluated by the method of Sarro et al. [G. B. De Sarro et al., Br. J. Pharmacol., 93, 247 (1988)]. That is, the compound dissolved in 10% 2-hydroxypropyl-$\beta$-cyclodextrin was administered intraperitoneally to DBA/2N type mice (male, 3 weeks old). After 20 minutes, a supersonic washer was used to apply audio stimulus of at least 90 dB for one minute. The wild running (WR), clonic seizures (clonus), tonic seizures (tonus), and respiratory arrest (RA) were observed. The seizure suppressing effect was evaluated from the rate of suppression of the average value of the seizure score found as 0=no response, 1=WR, 2=clonus, 3=tonus, and 4=RA. The results are shown in Table IV.

TABLE IV

| Compound No. | Antiseizure effect (suppression rate %) (compound 10 mg/kg, i.p.) |
|---|---|
| 17 | 88 |
| 18 | 62 |
| 19 | 52 |
| 20 | 91.3 |
| 21 | 91.3 |
| 22 | 72 |
| 23 | 84 |
| 24 | 74 |
| 25 | 54 |
| 27 | 52 |
| 28 | 56 |
| 29 | 68 |
| 34 | 80 |
| 35 | 98 |
| 36 | 68 |
| 37 | 88 |
| 38 | 82 |
| 39 | 90 |
| 40 | 84 |
| 41 | 92 |
| 42 | 72 |
| 43 | 90 |
| 44 | 68 |
| 45 | 82 |
| 46 | 82 |
| 47 | 78 |
| 48 | 82 |
| 49 | 50 |
| 50 | 56 |
| 53 | 74 |
| 54 | 58 |
| 55 | 71.7 |
| 57 | 60 |
| 58 | 51.7 |

INDUSTRIAL APPLICABILITY

As explained above, the arylpiperidinol or arylpiperidine derivatives represented by the formula (I) in the present invention have an effect suppressing cytotoxic $Ca^{2+}$ overload with high safety, and are useful as pharmaceuticals for the alleviation or treatment of ischemic diseases.

What is claimed is:

1. A compound having the formula (I'):

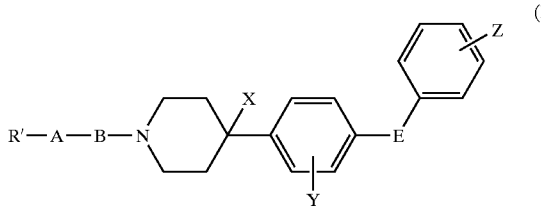

wherein, R' is an optionally substituted phenyl group, an optionally substituted phenoxy group, or an optionally substituted benzoyl group, A is a connecting bond, B is an alkylene group optionally substituted with a hydroxyl group or an alkoxy group, E is a connecting bond or a methylene group, X is a hydroxyl group, and Y and Z may be the same or different from each other and represent a hydrogen atom, a halogen atom, an alkoxy group, or an alkyl group optionally substituted with a halogen atom, provided that, when X is a hydroxyl group and R' is an optionally substituted phenoxy group, B is not an unsubstituted alkylene group, and that, when X is a hydroxyl group, R is an optionally substituted phenyl group, and A is a connecting bond, B is not an unsubstituted alkylene group, and its pharmaceutically acceptable salt.

2. A compound and its pharmaceutically acceptable salt as claimed in claim 1, wherein, in the formula (I'), R', A, B, and X are selected from the group consisting of:
   1) R' is an optionally substituted phenyl group, A is a connecting bond, B is an alkylene group substituted with a hydroxyl group, and X is a hydroxyl group;
   2) R' is an optionally substituted phenoxy group, A is a connecting bond, B is an alkylene group substituted with a hydroxyl group, and X is a hydroxyl group; and
   3) R' is an optionally substituted benzoyl group, A is a connecting bond, B is an alkylene group optionally substituted with a hydroxyl group or an alkoxy group, and X is a hydroxyl group where further E is a connecting bond or a methylene group, Y and Z may be the same or different from each other and represent a hydrogen atom, a halogen atom, an alkoxy group, or an alkyl group optionally substituted with a halogen atom.

3. A compound and its pharmaceutically acceptable salt as claimed in claim 1, wherein, in the formula (I'), R' is an optionally substituted benzoyl group, A is a connecting bond, and X is a hydroxyl group.

4. A compound and its pharmaceutically acceptable salt as claimed in claim 1, wherein, in the formula (I'), R' is an optionally substituted phenyl group, A is a connecting bond, B is a dimethylene group substituted with a hydroxyl group, and X is a hydroxyl group.

5. A compound and its pharmaceutically acceptable salt as claimed in claim 1, wherein, in the formula (I'), R' is an optionally substituted phenoxy group, A is a connecting bond, B is a trimethylene group substituted with a hydroxyl group, and X is a hydroxyl group.

6. A compound and its pharmaceutically acceptable salt as claimed in claim 1, wherein, in the formula (I'), R' is an optionally substituted benzoyl group and A and E are connecting bonds.

7. A pharmaceutical composition containing as an effective ingredient, the compound having the formula (I') according to claim 1 and its pharmaceutically acceptable salt.

8. A compound having the formula (II):

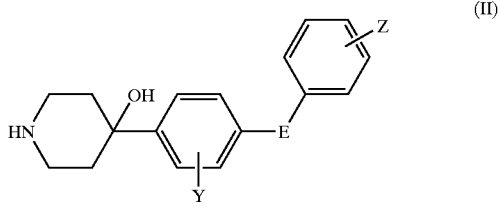

wherein, E' is a methylene group, and Y and Z may be the same or different from each other and represent a hydrogen atom, a halogen atom, an alkoxy group, or an alkyl group optionally substituted with a halogen atom.

9. A method for alleviation or treatment of symptoms due to ischemic diseases or symptoms derived from seizures, epilepsy and migraine, comprising administering to a patient in need of such treatment a compound as recited in claim 1 in an amount effective for the alleviation or treatment of said symptoms.

* * * * *

UNITED STATES PATENT AND TRADEMARK OFFICE
CERTIFICATE OF CORRECTION

PATENT NO. : 6,706,734 B2  
DATED : March 16, 2004  
INVENTOR(S) : Hirokazu Annoura et al.

It is certified that error appears in the above-identified patent and that said Letters Patent is hereby corrected as shown below:

Column 44,  
Table 1 (Continued), please delete the chemical structure for Compound 46 as shown below:

" 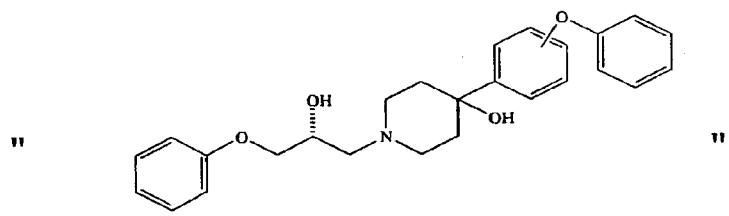 "

and insert the following chemical structure for Compound 46

-- 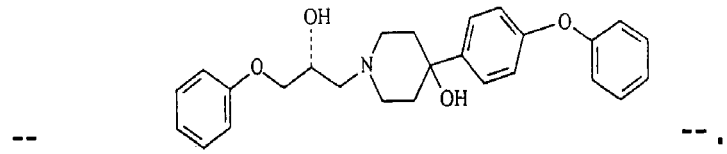 --.

Signed and Sealed this

Fifth Day of October, 2004

JON W. DUDAS  
*Director of the United States Patent and Trademark Office*